US009353163B2

(12) United States Patent
Stevis et al.

(10) Patent No.: US 9,353,163 B2
(45) Date of Patent: May 31, 2016

(54) APELIN FUSION PROTEINS AND USES THEREOF

(71) Applicant: REGENERON PHARMACEUTICALS, INC., Tarrytown, NY (US)

(72) Inventors: Panayiotis Stevis, West Orange, NJ (US); Andrew Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/212,753

(22) Filed: Mar. 14, 2014

(65) Prior Publication Data

US 2014/0275489 A1    Sep. 18, 2014

Related U.S. Application Data

(60) Provisional application No. 61/786,172, filed on Mar. 14, 2013, provisional application No. 61/906,567, filed on Nov. 20, 2013.

(51) Int. Cl.

| *A61K 39/00* | (2006.01) |
| *C12N 5/07* | (2010.01) |
| *C12N 15/00* | (2006.01) |
| *C12P 21/08* | (2006.01) |
| *C07H 21/04* | (2006.01) |
| *C07K 14/435* | (2006.01) |
| *C07K 14/47* | (2006.01) |
| *A61K 38/00* | (2006.01) |

(52) U.S. Cl.
CPC .............. *C07K 14/435* (2013.01); *C07K 14/47* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 6,492,324 | B1 * | 12/2002 | Hinuma et al. ................ 514/3.8 |
| 7,736,646 | B2 | 6/2010 | Krieg |
| 8,637,641 | B2 * | 1/2014 | Dahiyat et al. ............. 530/387.1 |
| 8,841,416 | B2 | 9/2014 | Ledbetter et al. |
| 2002/0062488 | A1 | 5/2002 | Doms et al. |
| 2004/0219152 | A1 | 11/2004 | Krieg |
| 2005/0075275 | A1 | 4/2005 | Albrecht et al. |
| 2005/0186662 | A1 * | 8/2005 | Low .............................. 435/69.4 |
| 2006/0045880 | A1 | 3/2006 | Krieg |
| 2006/0159676 | A1 | 7/2006 | Krieg |
| 2009/0233854 | A1 | 9/2009 | Fujii |
| 2010/0221255 | A1 | 9/2010 | Cuttitta et al. |
| 2011/0305692 | A1 * | 12/2011 | Hamblin et al. ............ 424/133.1 |
| 2013/0196899 | A1 * | 8/2013 | Zecri et al. .................... 514/1.9 |

| 2015/0252107 | A1 | 9/2015 | Stevis et al. |

FOREIGN PATENT DOCUMENTS

| EP | 1040189 B1 | 1/2008 |
| EP | 1613348 B1 | 6/2010 |
| WO | WO 02/36762 A1 | 5/2002 |
| WO | WO 2005/106493 A1 | 11/2005 |
| WO | WO 2010/053545 A2 | 5/2010 |
| WO | WO 2011/140086 A2 | 11/2011 |
| WO | WO 2012/125408 A1 | 9/2012 |
| WO | WO 2012/133825 A1 | 10/2012 |
| WO | WO 2013/012855 A1 | 1/2013 |
| WO | WO 2014/099984 A1 | 6/2014 |
| WO | WO 2014/152955 A1 | 9/2014 |
| WO | WO 2015/077491 A1 | 5/2015 |

OTHER PUBLICATIONS

Beck et al., "Therapeutic Fc-fusion proteins and peptides as successful alternatives to antibodies," mAbs, Landes Bioscience, 3(5):415-416, (2011).
Carter, "Introduction to current and future protein therapeutics: A protein engineering perspective," Experimental Cell Research, Academic Press, US, 317(9):1261-1269, (2011).
Cayabyab et al., "Apefin, the Natural Ligand of the Orphan Seven-Transmembrane Receptor APJ, Inhibits Human Immunodeficiency Virus Type Entry," J. Virol., 74(24):11972-11976, (2000).
Charo et al., "Endogenous regulation of cardiovascular function by apelin-APJ," Am J Physiol Heart Circ Physiol, 297:H1904-H1913, (2009).
Chen et al., "Apelin is a marker of the progression of liver fibrosis and portal hypertension in patients with biliary atresia," Pediatr Surg Int, 29:79-85, (2013).
Cheng et al., "Neuroprotection of apelin and its signaling pathway," Peptides, 37:171-173, (2012).
Claing et al., "Endocytosis of G protein-coupled receptors: roles of G protein-coupled receptor kinases and β-arrestin proteins," Progress in Neurobiology, 66:61-79, (2002).
Hosoya et al., "Molecular and Functional Characteristics of APJ," The Journal of Biological Chemistry, 275(28):21061-21067, (2000).
Huang et al., "Receptor-Fc fusion therapeutics, traps, and MIMETIBODY™ technology," Current Opinion in Biotechnology, 20(6):692-699, (2009).
Iturrioz et al., "By Interacting with the C-terminal Phe of Apelin, Phe255 and Trp259 in Helix VI of the Apelin Receptor Are Critical for Internalization," The Journal of Biological Chemistry, 285(42):32627-32637, (2010).
Japp et al., "Vascular Effects of Apelin in Vivo in Man," Journal of the American College of Cardiology, 52(111:908-913, (2008).
Jia et al., "Cardiovascular effects of a PEGylated apelin," Peptides, 38:181-188, (2012).

(Continued)

*Primary Examiner* — Marianne P Allen
(74) *Attorney, Agent, or Firm* — Alston & Bird LLP; Mary C. Johnson

(57) ABSTRACT

The invention provides a fusion protein or polypeptide comprising an apelin peptide fused to a multimerizing component. The invention also provides a fusion protein or polypeptide comprising an apelin peptide fused to an Fc domain, a fragment of an Fc domain, or a variant of an Fc domain. Apelin Fc-fusion polypeptides are capable of binding to the apelin receptor (APLNR). Apelin Fc-fusion polypeptides are capable of activating the APLNR and have improved pharmacokinetic properties compared to apelin peptides that are not fused to an Fc or an Fc fragment. Apelin Fc-fusion polypeptides are useful in diseases and conditions related to cardiovascular function, diabetes, cancer, obesity and other apelin-related conditions.

15 Claims, 7 Drawing Sheets

(56) References Cited

OTHER PUBLICATIONS

Lee et al., "Characterization of Apelin, the Ligand for the APJ Receptor," J. Neurochem., 74:34-41, (2000).

Lee et al., "Modification of the Terminal Residue of Apelin-13 Antagonizes Its Hypotensive Action," Endocrinology, 146:231-236, (2005).

Lee et al., "The fate of the internalized apelin receptor is determined by different isoforms of apelin mediating differential interaction with p-arrestin," Biochemical and Biophysical Research Communications, 395:185-189, (2010).

Lee et al., "Unravelling the roles of the apelin system: prospective therapeutic applications in heart failure and obesity," Trends in Pharmacological Sciences, 27(4):190-194, (2006).

Li et al., "Heterodimerization of human apelin and kappa opioid receptors: Roles in signal transduction," Cellular Signalling, 24:991-1001, (2012).

Lo et al., "High level expression and secretion of Fc-X fusion proteins in mammalian cells," Protein Engineering, 11(6):495-500, (1998).

Maguire et al., "[Pyr1] Apelin-13 Identified as the Predominant Apelin Isoform in the Human Heart : Vasoactive Mechanisms and Inotropic Action in Disease," Hypertension, 54:598-604, (2009).

Masri et al., "Apelin signalling: a promising pathway from cloning to pharmacology," Cellular Signalling, 17:415-426, (2005).

Medhurst et al., "Pharmacological and immunohistochemical characterization of the APJ receptor and its endogenous ligand apelin," J. Neorochem., 84:1162-1172, (2003).

Messari et al., "Functional dissociation of apelin receptor signaling and endocytosis: implications for the effects of apelin on arterial blood pressire," J. Neurochem., 90:1290-1301, (2004).

Murza et al., "Elucidation of the Structure-Activity Relationships of Apelin: Influence of Unnatural Amino Acids on Binding, Signaling, and Plasma Stability," ChemMedChem, 7(2):318-325, (2012).

Nishimura et al., "A novel system for the preparation of orphan receptor ligand peptides," J. Chem. Soc., Perkin Trans. 1, Royal Society of Chemistry, GB, 16:1960-1968, (2001).

Pisarenko et al., "Effects of structural analogues of apelin-l2 in acute myocardial infarction in rats," J Pharmacol Pharmacother, Epub before print, 13 pages, (2013).

Pisarenko et al., "In Vivo Reduction of Reperfusion Injury to the Heart with Apelin-12 Peptide in Rats," Bulletin of Experimental Biology and Medicine, 152(1):79-82, (2011). [Translated from Byulleten' Eksperimental'noi Biologii i Meditsiny, 152(7):86-89, (2011).]

Sato et al., "Therapeutic peptides: technological advances driving peptides into development", Current Opinion in Biotechnology, GB, 17(6): 638-642, (2006).

Sidorova et al., "Synthesis and Cardioprotective Properties of Apelin-12 and its Structural Analogues," Russian Journal of Bioorganic Chemistry, 38(1):30-411, (2012).

Sun et al., "Non-activated APJ suppresses the angiotensin II type 1 receptor, whereas apelin-activated APJ acts conversely," Hypertension Research, 34:701-706, (2011).

Wang et al., "Loss of Apelin Exacerbates Myocardial Infarction Adverse Remodeling and Ischemia reperfusion Injury: Therapeutic Potential of Synthetic Apelin Analogues," J Am Heart Assoc., 2:e000249, doi: 10.1161/JAHA.113.000249, 34 pages, (2013).

Murza et al., "Stability and Degradation Patterns of Chemically Modified Analogs of Apelin-13 in Plasma and Cerebrospinal Fluid," Peptide Science, 102(4):297-303, (2014).

Siddiquee et al., "The apelin receptor inhibits the angiotensin II type I receptor via allosteric trans-inhibition," Br J Pharmacol, Epub before print, doi: 10.1111/j.1476-5381.2012.02192.x, 168(5):1104-1117, (2013).

Vickers et al., "Hydrolysis of Biological Peptides by Human Angiotensin-Converting Enzyme-Related Carboxpeptidase (ACE2)," J Biol Chem, 277:14838-14843, (2002).

Zhang et al., "Identifying structural determinants of potency for analogs of apelin-13: Integration of C-terminal truncation with structure-activity," Bioorg & Med. Chem., 22:2992-2997, (2014).

"Product Datasheet: Anti APJ Receptor antibody ab66218," Abcam plc, 2 pages, (2013). [Retrieved from the Internet Feb. 24, 2015: <URL: http://www.abcam.com/APJ-Receptor-antibody-ab66218.pdf>]. [Author Unknown].

"Product Datasheet: Anti APJ Receptor antibody ab97464," Abcam plc, 2 pages, (2013). [Retrieved from the Internet Feb. 24, 2015: <URL: http://www.abcam.com/APJ-Receptor-antibody-ab97464.pdf>]. [Author Unknown].

"Product Datasheet: Anti-APJ Receptor antibody ab84296," Abcam plc, 4 pages, (2013). [Retrieved from the Internet Feb. 24, 2015: <URL: http://www.abcam.com/APJ-Receptor-antibody-ab84296.pdf>]. [Author Unknown].

"Product Datasheet: Anti-APJ Receptor antibody ab97452," Abcam plc, 2 pages, (2013). [Retrieved from the Internet Feb. 24, 2015: <URL: http://www.abcam.com/APJ-Receptor-antibody-ab97452.pdf>]. [Author Unknown].

Kidoya et al., "Spatial and temporal role of the apelin/APJ system in the caliber size regulation of blood vessels during angiogenesis," The EMBO Journal, 27:522-534, (2008).

Kidoya et al., "The apelin/APJ system induces maturation of the tumor vasculature and improves the efficiency of immune therapy," Oncogene, 31:3254-3264, (2012).

Pitkin et al., "Modulation of the apelin/APJ system in heart failure and atherosclerosis in man," British Journal of Pharmacology, 160:1785-1795, (2010).

\* cited by examiner

FIG. 1A

SEQ ID NO: 2

DKTHTCPPCPAPELLGGPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
DELTKNQVSLTCLVKGFYPSDIAVEWESNGQPENNYKTTPPVLDS
DGSFFLYSKLTVDKSRWQQGNVFSCSVMHEALHNHYTQKSLSLSP
GK*GGGGSGGGGSGGGGS*QRPRLSHKGPMPF

FIG. 1B

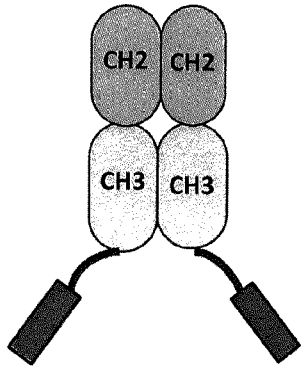

*Secreted Fc-Apelin Dimer*

N'-Fc-[linker]-Apelin-C'

FIG. 2A

SEQ ID NO: 4

QRPRLSHKGPMPFGGGGSGGGGSGGGGSDKTHTCPPCPAPELLGGP

SVFLFPPKPKDTLMISRTPEVTCVVVDVSHEDPEVKFNWYVDGVEV

HNAKTKPREEQYNSTYRVVSVLTVLHQDWLNGKEYKCKVSNKALPA

PIEKTISKAKGQPREPQVYTLPPSRDELTKNQVSLTCLVKGFYPSD

IAVEWESNGQPENNYKTTPPVLDSDGSFFLYSKLTVDKSRWQQGNV

FSCSVMHEALHNHYTQKSLSLSPGK

FIG. 2B

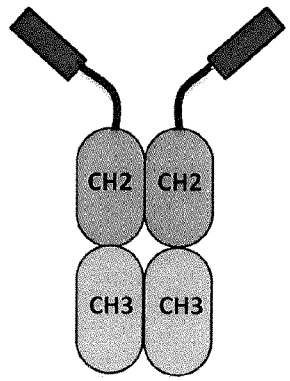

*Secreted Apelin-Fc Dimer*

N'-Apelin-[linker]-Fc-C'

| Treatment | EC$_{50}$ |
|---|---|
| Apelin13 DR/Forskolin (5μM) | 36.5 pM |
| hFc.Apelin13 DR/Forskolin (5μM) | 174 pM |
| Apelin13.hFc DR/Forskolin (5μM) | 22.1 nM |

APELIN FUSION PROTEINS AND USES THEREOF

CROSS-REFERENCE TO RELATED APPLICATIONS

This application claims the benefit under 35 USC §119(e) of U.S. Provisional Patent Application No. 61/786,172, filed 14 Mar. 2013, and claims the benefit under 35 USC §119(e) of U.S. Provisional Patent Application No. 61/906,567, filed 20 Nov. 2013, which applications are each specifically incorporated herein by reference in their entirety.

SEQUENCE LISTING

This application incorporates by reference the Sequence Listing submitted in Computer Readable Form as file 8050US_ST25.txt created on Mar. 12, 2014 (43,420 bytes).

FIELD OF THE INVENTION

The present invention relates to fusion proteins engineered with multimerizing components, such as human immunoglobulin Fc domains, fused to the N-terminus or C-terminus of apelin peptides. Recombinant proteins of the invention and compositions thereof, are useful in treating cardiovascular disease, ischemia-reperfusion, diabetes, and other apelin-related therapies.

BACKGROUND OF THE INVENTION

Preproapelin is a 77 amino acid protein expressed in the human CNS and peripheral tissues, e.g. lung, heart, and mammary gland. Peptides comprising C-terminal fragments of varying size of apelin peptide were shown to activate the G protein-coupled receptor, APJ receptor (Habata, et al., 1999, *Biochem Biophys Acta* 1452:25-35; Hosoya, et al., 2000, JBC, 275(28):21061-67; Lee, et al., 2000, *J Neurochem* 74:34-41; Medhurst, et al., 2003, *J Neurochem* 84:1162-1172). Many studies indicate that apelin peptides and analogues convey cardiovascular actions through their interaction with the APJ receptor (also known as APLNR), such as endothelium-dependent vasodilation (Tatemoto et al., 2001, *Regul Pept* 99:87-92), positive inotropic actions (Szokodi et al., 2002, *Circ Res* 91:434-440; Maguire, et al., 2009, *Hypertension* 54:598-604, epub before print on Jul. 13, 2009) and myocardial regional ischemia and reperfusion (Pisarenko, et al., 2013, *J Pharmacol Pharmacother*. "Effects of structural analogues of apelin-12 in acute myocardial infarction in rats", epub before print). Apelin-13, in particular, is a potent inotrope which could provide a treatment for heart failure by increasing heart contractility (Dai, et al., 2006, *Eur J Pharmacol* 553(1-3): 222-228; Maguire, et al, 2009, *Hypertension*. 54:598-604).

Transcriptional profiling of pre- and post-surgical ventricle tissue in human patients revealed that APLNR was the most significantly upregulated gene (Chen et al, 2003, *Circulation*, 108:1432-39). Apelin (apelin$^{-/-}$) and APJ (APJ$^{-/-}$) knockout studies in mice suggest that lack of an endogenous apelin-APJ pathway leads to a decreased ability to respond to cardiovascular stress, such as exercise (Charo et al., 2009, *Am J. Physiol. Heart Circ. Physiol.*, 297:H1904-1913).

Apelin has also been reported in the regulation of insulin and mechanisms of diabetes and obesity-related disorders. In mouse models of obesity, apelin is released from adipocytes and is directly upregulated by insulin (Boucher, et al., 2005, *Endocrinol* 146:1764-71). Apelin knockout mice demonstrate diminished insulin sensitivity (Yue, et al., 2010, *Am J Physiol Endocrinol Metab* 298:E59-E67).

APLNR-modulating agents also find utility in HIV treatment, since synthetic apelin peptides inhibited HIV-1 entry into CD4-APLNR-expressing cells (Cayabyab, M., et al., 2000, *J. Virol*. 74: 11972-11976). Furthermore, APLNR inhibitors, i.e. capable of blocking pathological angiogenesis, may be useful in inhibiting tumor growth or vascularization in the retina (Kojima, Y. and Quertermous, T., 2008, *Arterioscler Thromb Vasc Biol;* 28; 1687-1688; Rayalam, S. et al. 2011, *Recent Pat Anticancer Drug Discov* 6(3):367-72). Apelin neuroprotection is also seen where apelin-13, apelin-17 and apelin-36 act through signaling pathways to promote neuronal survival (Cheng, B, et al., 2012, *Peptides* 37(1):171-3).

APLNR binding agents are useful in ameliorating cardiovascular disease, as well as cancer, and diabetes, among other apelin related diseases. Since apelin peptides are rapidly cleared from the circulation and have a short plasma half-life of no more than eight minutes (Japp, et al, 2008, *J of Amer College Cardiolog,* 52(11):908-13), apelin is currently dosed continuously to see a therapeutic effect.

There is a need in the art for improved apelin binding agents as therapeutic agents, particularly those having extended half-life, while maintaining APLNR binding activity.

SUMMARY OF THE INVENTION

The present invention provides apelin fusion proteins, such as apelin fused to an Fc domain, engineered to deliver biologically active apelin peptides. In particular, apelin fusion proteins have improved pharmacokinetic properties compared to wild-type apelin peptides while maintaining APLNR activity.

One aspect of the invention provides a polypeptide comprising an apelin peptide fused to a multimerizing component. In one embodiment, the multimerizing component comprises an amino acid sequence containing at least one cysteine residue. In another embodiment, the multimerizing component comprises an amino acid sequence containing a leucine zipper, a helix-loop motif, a coiled-coil motif, or an immunoglobulin-derived domain. In another embodiment, the multimerizing component comprises an amino acid sequence containing an Fc domain.

In a related aspect, the invention provides a polypeptide comprising an apelin peptide fused to an Fc domain, a fragment of an Fc domain, or variant of an Fc domain. In some cases, the polypeptide can be part of a higher order structure, such as a protein or multimeric complex. In some embodiments, the apelin peptide is fused to the Fc domain, or fragment thereof, via one or more peptide linkers. In other embodiments, the apelin peptide is fused to the C-terminus of said Fc domain, or the apelin peptide is fused to the N-terminus of said Fc domain, or fragment thereof.

In one embodiment, the Fc domain of any of the apelin fusion proteins described herein comprises an immunoglobulin CH2 domain or an immunoglobulin CH3 domain. In another embodiment, the Fc domain comprises an immunoglobulin CH2 and CH3 domain. In some embodiments, the Fc domain is selected from the group consisting of IgG1 CH2 and CH3 domain, IgG4 CH2 and CH3 domain, IgG1 CH2 and an IgG4 CH3 domain, and IgG4 CH2 and an IgG1 CH3 domain. In other embodiments, the Fc domain comprises an IgG hinge domain. In still other embodiments, the Fc domain comprises an IgG hinge domain selected from the group consisting of SEQ ID NO: 14, SEQ ID NO: 17, SEQ ID NO: 18, SEQ ID NO: 21, and SEQ ID NO: 22.

In another embodiment, the polypeptide comprises a monomeric fusion polypeptide capable of forming a dimer. In some embodiments, the fusion polypeptide forms at least one disulfide bond with a second polypeptide.

In another related aspect, the invention provides an apelin receptor (APNLR) binding molecule comprising: an apelin peptide component, a human IgG Fc domain, and at least one linker component. In some embodiments, the apelin receptor (APNLR) binding molecule is an APLNR agonist, and in other cases the apelin receptor (APNLR) binding molecule is an APLNR antagonist.

In another aspect of the invention, an apelin fusion polypeptide or an apelin receptor binding molecule is provided that has a plasma or serum in vivo half-life of at least about 1 hour, or at least about 2, 3, 4, 5, 6, 7, 8, 9, or 10 or more hours.

In some embodiments, the apelin fusion polypeptide or receptor binding molecule of the invention comprises an apelin peptide selected from the group consisting of apelin42-77 (apelin-36), apelin61-77 (apelin-17), apelin63-77 (apelin-15), apelin64-77 (apelin-14), apelin65-77 (apelin-13), apelin66-77 (apelin-12), apelin67-77 (apelin-11), apelin68-77 (apelin-10), apelin73-77 (apelin-5), apelin61-76 (apelin-K16P), apelin61-75 (apelin-K15M), apelin61-74 (apelin-K14P), apelin-F13A, apelin65-76, apelin65-75, apelin66-76, apelin67-76, apelin66-75, apelin 67-75, and [Pyr$^1$]Apelin-13.

In certain aspects, the apelin fusion polypeptide or apelin receptor binding molecule is a serum stable protein. In some embodiments, the polypeptide has 95%, or 96%, or 97%, or 98%, or 99% or greater sequence identity to the amino acid sequence comprising SEQ ID NO: 2 or SEQ ID NO: 4. In other aspects, the polypeptide comprises an amino acid sequence at least 99% identical to SEQ ID NO: 2 or SEQ ID NO: 4. In other aspects, the polypeptide has an amino acid sequence comprising SEQ ID NO: 2 or SEQ ID NO: 4. In still other aspects, the polypeptide has an amino acid sequence selected from the group consisting of SEQ ID NO: 39, SEQ ID NO: 40 and SEQ ID NO: 41.

In certain aspects, the invention provides a recombinant polypeptide, wherein the polypeptide comprises N'—P1$_m$-X1$_n$-X2-X3-P2-A1-C', wherein: N' is the N-terminus and C' is the C-terminus of the polypeptide; P1 is a peptide linker; X1 comprises an IgG hinge domain; X2 comprises an IgG CH2 domain; X3 comprises an IgG CH3 domain, P2 is a peptide linker; and A1 is an amino acid sequence comprising a human apelin peptide, or a fragment or derivative thereof; wherein m=0 or 1, and n=0 or 1.

In certain aspects, the invention provides a recombinant polypeptide, wherein the polypeptide comprises N'-A1-P2-X1$_n$-X2-X3-C', wherein: N' is the N-terminus and C' is the C-terminus of the polypeptide; A1 is an amino acid sequence comprising a human apelin peptide, or a fragment or derivative thereof; P2 is a peptide linker; X1 comprises an IgG hinge domain; X2 comprises an IgG CH2 domain; and X3 comprises an IgG CH3 domain; wherein n=0 or 1.

In a second aspect, the invention provides a nucleic acid molecule encoding any apelin fusion polypeptide or apelin receptor binding molecule of the invention. In one embodiment, the nucleic acid molecule has a sequence selected from the group consisting of SEQ ID NO: 27 and SEQ ID NO: 28. In other embodiments, the nucleic acid molecule encodes for an amino acid sequence selected from the group consisting of SEQ ID NO: 2, SEQ ID NO: 4, SEQ ID NO: 39, SEQ ID NO: 40 and SEQ ID NO: 41.

In a third aspect, the invention provides vectors and cells comprising the nucleic acid molecules encoding an apelin fusion polypeptide or an apelin receptor binding molecule of the invention. In one embodiment, the vectors encode a nucleic acid molecule linked to a signal peptide sequence.

The invention also provides vectors encoding apelin fusion proteins comprising a nucleotide sequence encoding a signal peptide. The invention further provides vectors encoding apelin fusion proteins comprising a nucleotide sequence encoding a peptide linker fused to the C-terminus of a signal peptide placed upstream of the fusion protein.

In a fourth aspect, the invention provides a process for determining APLNR activity of a test molecule, contacting cells expressing APLNR, with the apelin fusion protein of the invention under the same test conditions as the test molecule, to determine whether the test molecule is an APLNR agonist or an APLNR antagonist.

In one embodiment, the invention provides a process for determining activation of an APLN receptor (APLNR) comprising: (a) contacting cells expressing APLNR with a test molecule, under conditions permitting the activation of the APLNR, (b) measuring APLNR activity, (c) separately contacting cells expressing APLNR with an apelin fusion protein of the invention under the same conditions as in step (a), (d) measuring APLNR activity of the cells in step (c) in the same manner as step (b), wherein the measurement of APLNR activity in step (b) compared to the measurement of APLNR activity in step (d) determines that the test molecule activates the APLNR.

Another aspect of the invention provides a method of making a fusion protein comprising apelin, said method comprising: (a) transfecting a host cell with a nucleic acid molecule encoding the fusion protein, wherein the nucleic acid molecule comprises a nucleotide sequence encoding a signal peptide, fused to either i) a nucleotide sequence encoding an Fc domain of human IgG linked to a nucleotide sequence encoding an apelin peptide, at the N-terminus of said apelin peptide, or ii) a nucleotide sequence encoding an apelin peptide linked to a nucleotide sequence encoding an Fc domain of a human IgG, at the N-terminus of said Fc domain, and (b) making the fusion protein by expressing the nucleic acid molecule of (a) in the host cell. The invention provides host cells secreting the fusion proteins of the invention into the cell culture medium.

In yet another aspect, the invention provides a method for treatment of a disease or condition related to apelin in a subject in need thereof, the method comprising administering to the subject a therapeutically effective amount of the apelin fusion proteins of the invention. The invention also provides a method for treating the disease or condition selected from the group consisting of cardiovascular disease, acute decompensated heart failure, congestive heart failure, myocardial infarction, cardiomyopathy, ischemia, ischemia/reperfusion injury, pulmonary hypertension, diabetes, obesity, cancer, metastatic disease, fluid homeostasis, pathological angiogenesis, retinopathy, fibrosis, and HIV infection, the method comprising administering to the subject a therapeutically effective amount of the apelin fusion protein of the invention.

The invention further provides compositions and kits comprising an apelin fusion polypeptide or an apelin receptor binding molecule of the invention. In some embodiments, the kit comprises one or more containers filled with at least one apelin fusion protein or polypeptide of the invention.

BRIEF DESCRIPTION OF THE DRAWINGS

FIG. 1A depicts components of an hFc-Apelin fusion protein, such as the amino acid sequence of SEQ ID NO: 2. The sequence of SEQ ID NO: 2 consists of (from N-terminus to C-terminus) human IgG1 Fc (underlined), G4S repeat peptide linker (italicized), and Apelin-13 (double-underlined).

FIG. 1B represents a secreted Fc-Apelin fusion protein and its components in the form of a homodimer.

FIG. 2A depicts the components of an Apelin-hFc fusion protein, such as the amino acid sequence of SEQ ID NO: 4. The sequence of SEQ ID NO: 4 consists of (from N-terminus to C-terminus) Apelin-13 (double-underlined), G4S repeat peptide linker (italicized), and human IgG1 Fc (underlined).

FIG. 2B represents a secreted Apelin-Fc fusion protein and its components in the form of a homodimer.

DETAILED DESCRIPTION OF THE INVENTION

Figure 3A:
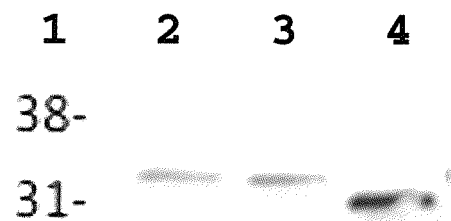
FIG. 3A illustrates the migration of Apelin Fc-fusion proteins and protein ladder control on an SDS-PAGE gel. Lane 1=protein marker measurements (31 and 38 kD); Lane 2=hFc-apelin-13 (SEQ ID NO: 2); Lane 3=apelin13-hFc protein (SEQ ID NO: 4); Lane 4=hFc only.

It is to be understood that this invention is not limited to particular methods, and experimental conditions described, as such methods and conditions may vary. It is also to be understood that the terminology used in this specification is for the purpose of describing particular embodiments only, and is not intended to be limiting, since the scope of the present invention is defined by the claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used in this application have the same meaning as commonly understood by one of ordinary skill in the art to which this invention belongs. Although any methods and materials similar or equivalent to those described in this specification can be used in the practice of the present invention, particular methods and materials are now described. All publications mentioned herein are incorporated herein by reference in their entirety.

Fusion Proteins

The term "immunoglobulin" (Ig) refers to a class of structurally related glycoproteins consisting of two pairs of polypeptide chains, one pair of light (L) chains and one pair of heavy (H) chains, which may all four be inter-connected by disulfide bonds. The structure of immunoglobulins has been well characterized. See for instance Fundamental Immunology Ch. 7 (Paul, W., ed., 2nd ed. Raven Press, N.Y. (1989)). Each heavy chain typically comprises a heavy chain variable region (abbreviated herein as $V_H$ or VH) and a heavy chain constant region ($C_H$ or CH). The heavy chain constant region typically comprises three domains, CH1, CH2, and CH3. The CH1 and CH2 domains are linked by a hinge. The Fc portion comprises at least the CH2 and CH3 domains.

Typically, the numbering of amino acid residues of immunoglobulins is according to IMGT, Sequences of Proteins of Immunological Interest, 5th Ed. Public Health Service, National Institutes of Health, Bethesda, Md. (1991), or by the EU numbering system of Kabat (also known as "EU numbering" or "EU index"), e.g., as in Kabat, E. A. et al. Sequences of Proteins of Immunological interest. $5^{th}$ ed. US Department of Health and Human Services, NIH publication No. 91-3242 (1991).

As used in the specification, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 500 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

The term "Fc" refers to a portion of a heavy chain constant region that comprises at least the CH2 and CH3 domains that typically bind to an Fc receptor e.g., an FcγR, namely FcγRI (CD64), FcγRII (CD32), FcγRIII (CD16) or an FcRn, i.e., a neonatal Fc receptor. If the CH2 and CH3 region contains deletions, substitutions, and/or insertions or other modifications that render it unable to bind any Fc receptor, then the CH2 and CH3 region is considered to be non-functional in terms of its typical biological function.

The phrase "fusion proteins", and specifically "apelin fusion proteins", includes recombinant polypeptides and proteins derived from apelin that have been engineered to contain a multimerizing component as described herein.

The phrase "Fc-fusion proteins", and specifically "apelin-Fc" or "Fc-apelin" fusion proteins, includes recombinant polypeptides and proteins derived from apelin that have been engineered to contain an Fc fragment as described herein. For example, an "apelin Fc-fusion protein" includes a chimeric protein comprising an amino acid sequence of an apelin peptide or analogue fused to an amino acid sequence of an Fc domain of Ig, either at the N-terminus or the C-terminus, with or without peptide linkers. Examples of peptides used in fusion proteins are known in the art (see e.g. Dumont, et al., 2006, *Biodrugs* 20(3):150-160). Fc-fusion proteins are also referred to in the art as immunoadhesins.

The phrase "fused to", as used herein, means (but is not limited to) a polypeptide formed by expression of a chimeric gene made by combining more than one sequence, typically by cloning one gene into an expression vector in frame with a second gene such that the two genes are encoding one continuous polypeptide. In addition to being made by recombinant technology, parts of a polypeptide can be "fused to" each other by means of chemical reaction, or other means known in the art for making custom polypeptides.

The term "protein" is meant to include quaternary structures, ternary structures and other complex macromolecules composed of at least one polypeptide. The term "protein" includes polypeptide.

As used herein, a "polypeptide" is a single linear polymer chain of amino acids bonded together by peptide bonds between the carboxyl and amino groups of adjacent amino acid residues. The term "protein" may also be used to describe a large polypeptide, such as a seven transmembrane spanning domain protein.

The polypeptides of the invention comprise amino acid sequences that are derived from an immunoglobulin domain. A polypeptide or amino acid sequence "derived from" a designated protein or polypeptide refers to the origin of the polypeptide. As used herein, "isotype" refers to the immunoglobulin class or subclass (for instance, IgG1, IgG2, IgG3, IgG4, IgD, IgA, IgE, or IgM) that is encoded by heavy chain constant region genes.

The phrase "heavy chain" or "immunoglobulin (Ig) heavy chain", as used herein, includes Ig heavy chain constant region sequence from any organism, and unless otherwise specified includes a heavy chain variable domain. Heavy chain variable domains include three heavy chain complementary determining regions (CDRs) and four framework regions (FRs), unless otherwise specified. Fragments of heavy chain variable domains include CDRs, or both CDRs and FRs. A typical heavy chain constant region (CH) has, following the variable domain, from N-terminal to C-terminal: a CH1 domain, a hinge, a CH2 domain, and a CH3 domain. A functional fragment of a heavy chain, e.g. in an antigen-binding protein, includes a fragment that is capable of specifically recognizing an antigen (e.g., recognizing the antigen with a $K_D$ in the micromolar, nanomolar, or picomolar range), that is capable of being expressed in and secreted from a cell, and that comprises at least one CDR.

Flow cytometry-based autologous secretion trap (FASTR) methods, which utilize a membrane-bound human Fcγ receptor (hFcγR) to capture co-secreted proteins, can be used to rapidly isolate high expression clones expressing or secreting an antibody or Fc-fusion protein. (See, US20090137416 A1, which is herein incorporated by reference.) Such high expression clones may be employed to isolate cells expressing proteins comprising an Fc-fusion protein as described herein. FASTR methods may be utilized to directly screen and isolate cells expressing any recombinant polypeptide or Fc-fusion protein of the invention.

The term "hinge", as used herein, is intended to include the region of consecutive amino acid residues that connect the C-terminus of the CH1 to the N-terminus of the CH2 domain of an immunoglobulin. Several amino acids of the N-terminus of the CH2 domain, which are coded by the CH2 exon, are also considered part of the "lower hinge". Without being bound by any one theory, amino acids of the hinge region of IgG1, IgG2 and IgG4 have been characterized as comprising 12-15 consecutive amino acids encoded by a distinct hinge exon, and several N-terminal amino acids of the CH2 domain (encoded by the CH2 exon) (Brekke, O. H., et al., 1995, *Immunology Today* 16(2):85-90). On the other hand, IgG3 comprises a hinge region consisting of four segments: one upper segment resembling the hinge region of IgG1, and 3 segments that are identical amino acid repeats unique to IgG3.

Amino acid residues derived from Ig domains, such as human IgG, are identified herein by the EU numbering system of Kabat, also known as "EU numbering" or the "EU index" (according to Kabat, E. A. et al. Sequences of Proteins of Immunological interest. 5$^{th}$ ed. US Department of Health and Human Services, NIH publication No. 91-3242, 1991, and updated according to the IMGT® Scientific Chart, IMGT, the international ImMunoGeneTics information System®, http://www.imgt.org/IMGTScientificChart/Numbering/Hu_IGHGnber.html, created: 17 May 2001, last updated: 10 Jan. 2013).

For example, EU numbering for human IgG1 hinge amino acids and the corresponding IMGT unique numbering convention, and the Kabat numbering convention (according to Kabat, E. A. et al, 1991, and IMGT® Scientific Chart supra) are listed in Table 1.

TABLE 1

IgG1 hinge numbering

| IgG1 (IGHG1) amino acids [SwissProt P01857] | IMGT Unique Numbering for the hinge | EU Numbering | Kabat Numbering |
| --- | --- | --- | --- |
| (E) | 1 | 216 | 226 |
| P | 2 | 217 | 227 |
| K | 3 | 218 | 228 |
| S | 4 | 219 | 232$^a$ [229]$^b$ |
| C | 5 | 220 | 233$^a$ [230]$^b$ |
| D | 6 | 221 | 234$^a$ [232]$^b$ |
| K | 7 | 222 | 235 |
| T | 8 | 223 | 236 |
| H | 9 | 224 | 237 |
| T | 10 | 225 | 238 |
| C | 11 | 226 | 239 |
| P | 12 | 227 | 240 |
| P | 13 | 228 | 241 |
| C | 14 | 229 | 242 |
| P | 15 | 230 | 243 |

Amino acids resulting from exon splicing are shown in parentheses.
$^a$numbering according to the last updated IMGT Scientific Chart
$^b$numbering according to EU index as originally reported in Kabat, EA, et al. 1991
See also, e.g., Lefranc, M.-P. et al., *Devel Comp Immunol*, 29, 185-203 (2005); and Edelman, G. M. et al. *PNAS USA*, 63: 78-85 (1969).

TABLE 2

IgG1 C-domain hinge numbering

| IgG1 (IGHG1) amino acids [SwissProt P01857] | IMGT Unique Numbering for C-domains | EU Numbering | Kabat Numbering |
| --- | --- | --- | --- |
| (A) | 1.6 | 231 | 244 |
| P | 1.5 | 232 | 245 |
| E | 1.4 | 233 | 246 |
| L | 1.3 | 234 | 247 |
| L | 1.2 | 235 | 248 |
| G | 1.1 | 236 | 249 |

In one embodiment, Fc-fusion proteins of the invention comprise an Fc domain or any Fc domain fragment or any Fc domain variant. In some embodiments, the Fc domain comprises an Ig CH2 and an Ig CH3 domain, or a fragment or variant thereof. In other embodiments, the Fc domain comprises an Ig hinge domain, or a fragment or variant thereof, an Ig CH2 domain or a fragment or variant thereof and an Ig CH3 domain or a fragment or variant thereof. In still other embodiments, the Fc domain comprises an Ig CH1 domain or a fragment or variant thereof, an Ig hinge domain or a fragment or variant thereof, an Ig CH2 domain a fragment or variant thereof, and an Ig CH3 domain a fragment or variant thereof.

The term "chimeric", as used herein, means composed of parts of different origin. The phrase "chimeric protein", which encompasses "chimeric polypeptides", includes a first amino acid polypeptide linked to a second amino acid polypeptide that is not normally linked in nature. The amino acid sequences may normally exist as separate polypeptides or in a different arrangement on the same polypeptide or protein, and are brought together in a fusion polypeptide in a new arrangement.

The Fc domain may be chimeric, combining Fc sequences derived from more than one immunoglobulin isotype. For example, a chimeric Fc domain can comprise part or all of a CH2 sequence derived from a human IgG1, human IgG2 or human IgG4 CH2 region, and part or all of a CH3 sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A chimeric Fc domain can have altered Fc receptor binding, which in turn affects Fc effector function.

For certain therapies, the Fc domain may be engineered to activate all, some, or none of the normal Fc effector functions, without affecting the desired Fc-fusion protein's pharmacokinetic properties. Therefore, engineered Fc domains that have altered Fc receptor binding may have reduced side effects. Thus, in one embodiment, the protein comprises a chimeric or otherwise modified Fc domain. For an example of a chimeric Fc domain, see U.S. Provisional Application No. 61/759,578, filed Feb. 1, 2013, which is herein incorporated in its entirety.

The invention also provides apelin Fc-fusion proteins comprising variant Fc domain sequences. Such "variant" Fc domains and Fc domain fragments comprise one or more additions, deletions, or substitutions of amino acids when compared to wild-type sequence, but essentially function as desired, e.g. exhibit APLNR activity and prolong half-life of the fusion protein, as described in this specification.

In some embodiments, the Fc domain comprises an IgG CH2 and CH3 domain. In other embodiments, the Fc domain comprises an IgG1 CH2 and CH3 domain, IgG4 CH2 and CH3 domain, IgG1 CH2 domain and an IgG4 CH3 domain, or IgG4 CH2 domain and an IgG1 CH3 domain. In some embodiments, the Fc domain is a chimeric Fc domain comprising a fragment selected from the group consisting of CH1 domain, hinge domain, CH2 domain and CH3 domain, wherein the fragment is derived from IgG1, IgG2, IgG3, IgG4, IgD, IgA, IgE, or IgM. In some embodiments, the chimeric Fc domain comprises a CH2 domain selected from the group consisting of SEQ ID NO: 15, SEQ ID NO: 19, and SEQ ID NO: 23. In some embodiments, the chimeric Fc domain comprises a CH3 domain selected from the group consisting of SEQ ID NO: 16, SEQ ID NO: 20, and SEQ ID NO: 24. In another embodiment, the Fc domain comprises a chimeric IgG CH2-CH3 domain. Accordingly, variants and fragments of such Fc domains are also part of this invention.

In one embodiment, the Fc domain comprises an IgG1, IgG2, IgG3 or IgG4 hinge domain. In one embodiment, the hinge domain comprises SEQ ID NO: 14, SEQ ID NO: 17, SEQ ID NO: 18, SEQ ID NO: 21 or SEQ ID NO: 22. In another embodiment, the Fc domain comprises a chimeric hinge domain. In another embodiment, the Fc domain comprises a chimeric hinge domain comprising a hinge fragment selected from the group consisting of SEQ ID NO: 14, SEQ ID NO: 18, and SEQ ID NO: 22.

According to certain embodiments of the present invention, Fc-fusion proteins are provided comprising an Fc domain comprising one or more mutations which enhance or diminish protein binding to the FcRn receptor, e.g., at acidic pH as compared to neutral pH. For example, the present invention includes Fc-fusion proteins comprising a mutation in the CH2 or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes Fc-fusion proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the fusion proteins disclosed herein, are contemplated within the scope of the present invention.

Modifications to the Fc domain of an Fc-fusion protein may confer increased stability, such as resistance to degradation. Fusion proteins may be modified using ordinary molecular biological techniques and synthetic chemistry so as to improve their resistance to proteolytic cleavage or resistance to metal ion-related cleavage. Analogues of such polypeptides include substitution variants made by the exchange of one amino acid for another or substitution with residues other than naturally occurring L-amino acids, e.g. D-amino acids or non-naturally occurring synthetic amino acids.

In one embodiment, Fc-fusion proteins of the invention comprise an apelin peptide fused to an Fc domain as described herein.

In some embodiments, the Fc-fusion protein of the invention activates the APLNR receptor and has a greater half-life than that of an apelin peptide that is not fused to an Fc domain, such as a greater half-life of more than eight minutes.

Apelin Ligand and Apelin Receptor

Apelin is produced endogenously as a prepropeptide of 77 amino acids which is cleaved to yield several shorter biologically active fragments, or apelin peptides.

In some embodiments, Fc-fusion proteins of the invention comprise an apelin peptide as described herein.

In some embodiments, the apelin peptide comprises a fragment or derivative of the preproapelin polypeptide (SEQ ID NO: 5).

"Apelin peptides" includes specific apelin fragments and derivatives known in the art, e.g., an apelin peptide comprising amino acids 6-77, 40-77, 42-77, 43-77, 47-77, 59-77, 61-77, 63-77, 64-77, 65-77, 66-77, 67-77, 73-77, 1-25, 6-25, 42-64, 61-64, 61-74, 61-75, 61-76, 65-76, 65-75, 66-76, 67-76, 66-75, 67-75, 42-58, 42-57, 42-56, 42-55, 42-54, 42-53, or pyroglutamylated apelin65-77 ([Pyr$^1$]Apelin-13), of the preproapelin polypeptide (SEQ ID NO: 5). See e.g. U.S. Pat. No. 6,492,324, issued on Dec. 10, 2002, and El Messari et al. 2004, *J Neurochem*, 90:1290-1301, which are both herein incorporated by reference. In one embodiment, the apelin peptide comprises amino acids 65-76, 65-75, 61-77, 63-77, 64-77, 65-77, 66-77, 67-77, 66-76, 67-76, 66-75, 67-75, or 42-77 of SEQ ID NO: 5.

It has been demonstrated herein that fragments of apelin peptides, for example peptides having C-terminal deletions, retain their cellular activities (see also El Messari et al. 2004, *J Neurochem*, 90:1290-1301). Certain apelin peptide derivatives, such as apelin peptides and fusions having additional one or more C-terminal amino acids, are shown herein to retain their cellular activities. As such, fragments and derivatives of the apelin peptides described in this specification are included in the invention. Other fragments and derivatives of apelin peptides may be made by recombinant technology by the skilled artisan.

In other embodiments, the apelin peptide is selected from the group consisting of apelin40-77 (apelin-38), apelin42-77 (apelin-36), apelin43-77 (apelin-35), apelin47-77 (apelin-31), apelin59-77 (apelin-19), apelin61-77 (apelin-17), apelin63-77 (apelin-15), apelin64-77 (apelin-14), apelin65-77 (apelin-13), apelin66-77 (apelin-12, or A12), apelin67-77 (apelin-11), apelin68-77 (apelin-10), apelin73-77 (apelin-5), apelin61-76 (apelin-K16P), apelin61-75 (apelin-K15M), apelin61-74 (apelin-K14P), and [Pyr$^1$]Apelin-13.

In still other embodiments, the apelin peptide is selected from the group consisting of apelin61-77 (apelin-17; SEQ ID NO: 7), apelin65-77 (apelin-13; SEQ ID NO: 6), apelin-F13A (SEQ ID NO: 29), apelin66-77 (apelin-12, or A12, SEQ ID NO: 32), apelin67-77 (apelin-11; SEQ ID NO: 33), apelin65-76 (SEQ ID NO:30), apelin65-75 SEQ ID NO: 31), apelin67-77 (SEQ ID NO: 6), apelin66-76 (SEQ ID NO: 34), apelin67-76 (SEQ ID NO: 35), apelin 66-75 (SEQ ID NO: 36), apelin 67-75 (SEQ ID NO: 37), and [Pyr$^1$]Apelin-13.

In some embodiments, the apelin peptide is modified to minimize degradation and to enhance serum stability. In certain embodiments, the modified apelin peptide is selected from the group consisting of SEQ ID NO: 38 (apelin-13+5G), SEQ ID NO: 42 (apelin-13+R), SEQ ID NO: 43 (apelin-13+S), and SEQ ID NO: 44 (apelin-13+H).

In one embodiment, the apelin peptide is selected from the group consisting of apelin-36 (SEQ ID NO: 8), apelin-17 (SEQ ID NO: 7), apelin-13 (SEQ ID NO: 6) and [Pyr$^1$] Apelin-13. In another embodiment, the apelin peptide comprises apelin-13 (SEQ ID NO: 6), or a fragment thereof.

Apelin peptides are rapidly cleared from the circulation and have a short plasma half-life of no more than eight minutes (Japp, et al, 2008, *J of Amer College Cardiolog*, 52(11): 908-13). Apelin fusion proteins of the invention have increased half-life compared to apelin peptides.

Included in the invention are analogues of apelin modified to include non-standard amino acids or modified amino acids. Such peptides containing non-natural, or natural but non-coded, amino acids may be synthesized by an artificially modified genetic code in which one or mode codons is assigned to encode an amino acid which is not one of the standard amino acids. For example, the genetic code encodes 20 standard amino acids, however, three additional proteinogenic amino acids occur in nature under particular circumstances: selenocysteine, pyrrolysine and N-Formyl-methionine (Ambrogelly, et al. 2007, *Nature Chemical Biology*, 3:29-35; Böck, A. et al, 1991, *TIBS*, 16 (12): 463-467; and Théobald-Dietrich, A., et al., 2005, *Biochimie*, 87(9-10):813-817). Post-translationally modified amino acids, such as carboxyglutamic acid (γ-carboxyglutamate), hydroxyproline, and hypusine, are also included. Other non-standard amino acids include, but are not limited to, citrulline, 4-benzoylphenylalanine, aminobenzoic acid, aminohexanoic acid, N$^\alpha$-methylarginine, α-Amino-n-butyric acid, norvaline, norleucine, alloisoleucine, t-leucine, α-Amino-n-heptanoic acid, pipecolic acid, α,β-diaminopropionic acid, α,γ-diaminobutyric acid, ornithine, allothreonine, homoalanine, homoarginine, homoasparagine, homoaspartic acid, homocysteine, homoglutamic acid, homoglutamine, homoisoleucine, homoleucine, homomethionine, homophenylalanine, homoserine, homotyrosine, homovaline, isonipecotic acid, β-Alanine, β-Amino-n-butyric acid, β-Aminoisobutyric acid, γ-Aminobutyric acid, α-aminoisobutyric acid, isovaline, sarcosine, naphthylalanine, nipecotic acid, N-ethyl glycine, N-propyl glycine, N-isopropyl glycine, N-methyl alanine, N-ethyl alanine, N-methyl β-alanine, N-ethyl β-alanine, octahydroindole-2-carboxylic acid, penicillamine, pyroglutamic acid, sarcosine, t-butylglycine, tetrahydro-isoquinoline-3-carboxylic acid, isoserine, and α-hydroxy-γ-aminobutyric acid. A variety of formats to expand the genetic code are known in the art and may be employed in the practice of the invention. (See e.g. Wolfson, W., 2006, *Chem Biol*, 13(10): 1011-12.)

Apelin analogues incorporating such non-standard amino acids or post-translational modifications can be synthesized by known methods. Exemplary apelin analogues include N$^\alpha$-methylarginine-apelin-A12 analogue, [Nle$^{75}$, Tyr]apelin-36, [Glp$^{65}$Nle$^{75}$, Tyr$^{77}$]apelin-13, (Pyr$^1$)[Met(O)11]-apelin-13, (Pyr$^1$)-apelin-13, [d-Ala$^{12}$]-A12, and N-alpha-acetyl-nona-D-arginine amide acetate.

Also included in the invention are analogues of the apelin component of an apelin fusion protein modified to be resistant to cleavage, for example cleavage by angiotensin converting enzyme 2 (ACE2). Such apelin analogues have been shown to have a marked increase in efficacy compared to unmodified apelin ligands in in vivo models of myocardial response to ischemia (Wang, et al. Jul. 1, 2013, *J Am Heart Assoc.* 2: e000249).

Such cleavage-protected apelin fusion proteins comprise apelin peptides that are modified to include substitution variants, i.e. variants made by the exchange of one amino acid for another at one or more cleavage sites within the protein. Such amino acid substitutions are envisioned to confer increased stability without the loss of other functions or properties of the protein. Other cleavage-protected apelin fusion proteins comprise apelin peptides modified to include terminal amide or acetyl groups. In some embodiments, cleavage-protected apelin fusion proteins comprise proteinogenic amino acids, non-standard amino acids or post-translationally modified amino acids. Still other cleavage-protected or cleavage-resistant apelin fusion proteins comprise modified apelin peptides that include one or more additional N-terminal amino acids. It is desirable that such modified apelin peptides do not alter the peptide's ability to activate the APLNR. Exemplary modified apelin peptides and fusion proteins of the invention that activate APLNR include SEQ ID NO: 38, SEQ ID NO: 39, SEQ ID NO: 40, SEQ ID NO: 41, SEQ ID NO: 42, SEQ ID NO: 43, and SEQ ID NO: 44.

Apelin, as mentioned above, is known to be a ligand of APLNR, a G protein-coupled receptor. The term "ligand", as used herein, means a molecule that binds to another molecule such as a receptor. A ligand molecule capable of binding to a G protein-coupled receptor (GPCR) is selected from the group consisting of an ion, small organic molecule, peptide, polypeptide, antibody, bispecific antibody, antibody fragment, protein, and large organic molecule. A ligand may be further characterized as, for example, an agonist, partial agonist, inverse agonist, antagonist, competitive antagonist, positive allosteric modulator or negative allosteric modulator depending on the state of activity it confers through the receptor to which it binds. For example, for agonists to bind to a GPCR, other molecular interactions that keep such GPCR in an inactive state are disrupted.

The term "agonist", as used herein, includes a moiety that interacts with (directly or indirectly binds) and activates a receptor, such as the APLNR receptor, and initiates a physiological or pharmacological response characteristic of that receptor, such as when bound to its endogenous ligand. For example, upon binding to a GPCR, moieties may activate an intracellular response, enhance GTP binding to cell membranes, or internalize the receptor. Such agonist moiety can be for example a protein, polypeptide, peptide, antibody, antibody fragment, large molecule, or small molecule.

The term "antagonist", as used herein, is intended to mean a moiety that competitively binds to the receptor at the same site as an agonist (for example, the endogenous ligand), but which does not activate the intracellular response initiated by the active form of the receptor, and thereby inhibits the intracellular response by an agonist or partial agonist. In some cases, antagonists do not diminish the baseline intracellular response in the absence of an agonist or partial agonist. An antagonist does not necessarily have to function as a competitive binding inhibitor, but may work by sequestering an agonist, or indirectly modulating a downstream effect.

G protein-coupled receptors (GPCRs), which are seven transmembrane domain receptors, typically transduce their cellular signals via heterotrimeric guanine nucleotide-binding proteins (G proteins), consisting of an alpha ($\alpha$), beta ($\beta$), and gamma ($\gamma$) subunit, whereas the $\alpha$ subunit contains a binding site for GTP/GDP, and the $\beta\gamma$ dimer is bound to the $\alpha$ subunit in an inactive state. G proteins are naturally occurring on the cytoplasmic side of the plasma membrane. Binding of an extracellular ligand leads to a conformational change in the receptor protein that allows it to make contact with a guanine-nucleotide binding protein (G protein), and thus enhance the exchange of GTP for GDP. Upon the exchange, the $\beta\gamma$ dimer dissociates from the $\alpha$ subunit. Both the activated $\alpha$ subunit and the $\beta\gamma$ dimer can influence intracellular effector proteins.

In general, GPCRs activate a particular G$\alpha$ protein subunit family, which leads to the activation or inactivation of a particular signal transduction pathway. The apelin receptor (APLNR) is a GPCR.

Upon interaction with a ligand or binding molecule, the apelin receptor (APLNR) triggers one or more of several intracellular signaling cascades including signaling initiated by: 1) inhibitory G protein subunit, G$\alpha_{i/o}$, 2) activation of ERKs through PKC, or 3) internalization of the GPCR. In other words, the pharmacological and/or physiological response of APLNR in its active state is determined by the downstream action of G$\alpha_i$ subunits (which, e.g., inhibit adenylyl cyclase), phosphorylated ERKs or internalized APLNR. It is understood that other intracellular effectors may be engaged by an activated APLNR.

Apelin receptor (APLNR) originally named APJ receptor (O'Dowd, et al., 1993, *Gene* 136(1-2):355-360), was isolated from human genomic DNA as a 380 amino acid 7-transmembrane domain orphan receptor. (See NCBI RefSeq No. NP_005152, which is herein incorporated by reference.) Apelin was shown to be the endogenous ligand for APLNR (APJ) when tissue extracts from bovine stomach revealed apelin peptides that stimulated acidification rate in CHO cells expressing APLNR (APJ) in a range from 0.1-100 nM (Tatemoto, et al., 1998, *Biochem Biophys Res Comm* 251:471-476).

The interaction between apelin and APLNR, and hence the interaction between apelin fusion proteins and APLNR, can be measured by a number of in vitro (e.g. as in a test tube or plate), ex vivo (e.g. as in a cell culture from a living animal) and in vivo (e.g. as in a living animal) bioassays known to the skilled person in the relevant art.

In some embodiments, APLNR agonists are selected from the group consisting of apelin-36, apelin-19, apelin-17, apelin-13, apelin-12, N$^\alpha$-methylarginine-apelin-A12 analogue, [Nle$^{75}$, Tyr]apelin-36, [Glp$^{65}$Nle$^{75}$, Tyr$^{77}$]apelin-13, (Pyr$^1$) [Met(O)11]-apelin-13, and (Pyr$^1$)-apelin-13.

In one embodiment, the apelin fusion polypeptide is an APLNR agonist selected from the group consisting of SEQ ID NO: 2, SEQ ID NO: 4, SEQ ID NO: 39, SEQ ID NO: 40 and SEQ ID NO: 41, and fragments or derivatives thereof.

Antagonists of the receptor are known to block the hypotensive action of the APLNR. The apelin peptide derivative made by modifying apelin-13 at its C-terminal phenylalanine (F) to alanine (A) (apelin-13(F13A); SEQ ID NO: 29) was described by Lee, et al. 2005 (Endocrinol 146(1):231-236) as a functional antagonist. The APLNR antagonist F13A was also reported to improve circulatory and renal function in cirrhotic animals, indicating that the antagonist may have mediated the overactive effects of an upregulated apelin system in pathogenic disease such as fibrosis of the liver (Principe, A., et al. 2008, *Hepatology*, 48(4):1193-1201). In some embodiments, APLNR antagonists are selected from the group consisting of apelin-13(F13A) (SEQ ID NO: 29), [d-Ala$^{12}$]-A12, cyclo(1-6)CRPRLC-KH-cyclo(9-14)CR-PRLC, and N-alpha-acetyl-nona-D-arginine amide acetate (ALX40-4C; CAS Registry No. 153127-49-2).

In another embodiment, the apelin fusion protein or polypeptide comprises an APLNR binding molecule. In other embodiments, the apelin fusion protein or polypeptide comprises an APLNR agonist. In some embodiments, the fusion polypeptide of the invention comprises an APLNR antagonist.

Receptor Assays

It is understood that receptor screening assays are employed not only to the subject apelin fusion proteins of the invention, but also any test compounds including agonists and antagonists of the APLNR. Many receptor screening assays to determine activation or inactivation of the APLNR are well-known in the art, and the following examples are not intended to limit the scope of what the inventors regard as their invention.

GPCR-mediated guanine nucleotide exchange is monitored by measuring [$^{35}$S]GTP$\gamma$S binding to plasma membranes prepared from cells expressing GPCRs of interest. The [$^{35}$S]GTP$\gamma$S assay is generally useful for Gi/o-coupled receptors because Gi/o is the most abundant G protein in most cells and has a faster GDP-GTP exchange rate than other G proteins (Milligan G., 2003, *Trends Pharmacol Sci*, 2003, 24:87-90). Commercially available Scintillation Proximity Assay (SPA™) kits allow measurement of desired [$^{35}$S]GTP$\gamma$S-bound $\alpha$ subunit (Perkin Elmer, Waltham, Mass., USA).

Activation of Gi/o-coupled receptors results in decreased adenylyl cyclase activity and therefore inhibition of cAMP in the cell, via the G alpha subunits Gi or Go. To maximize the inhibition signal, forskolin (a direct activator of adenylate cyclase) is typically utilized to stimulate adenylyl cyclase in the assay, and thus cAMP, thereby rendering the inhibition signal more easily detectable. Radiometric GE Healthcare SPA™ (Piscataway, N.J., USA) and Perkin Elmer Flash-Plate™ cAMP assays are available, as well as fluorescence or luminescence-based homogenous assays (e.g. PerkinElmer AlphaScreen™, DiscoveRx HitHunter™ (Fremont, Calif., USA), and Molecular Devices FLIPR® (Sunnyvale, Calif., USA)) to measure accumulation of intracellular cAMP.

The action of GPCRs that modulate cAMP levels, like APLNR, may be linked to luciferase transcription in a cell by a cAMP response element (CRE). A CRE-luc construct (CRE-responsive luciferase) encodes a luciferase reporter gene under the control of a promoter and tandem repeats of the CRE transcriptional response element (TRE). Following activation of the receptor, cAMP accumulation in the cell is measured by the amount of luciferase expressed in the cell following addition of chemiluminescent detection reagents. For APLNR, and other Gi-coupled receptors, forskolin is added to induce cAMP and a decrease in CRE activity (chemiluminescence) indicates GPCR activation. Various commercial kits are available, such as from Promega (Madison, Wis., USA), SABiosciences (A Qiagen Company, Valencia, Calif., USA), etc.

In some instances, agonist binding to the receptor may initiate arrestin-mediated signaling, without triggering G protein-mediated signaling or slow down G protein-mediated signaling. Beta-arrestin (β-arrestin) interaction with GPCRs at the cell-surface can uncouple heterotrimeric G proteins to the receptor and lead to other cell signaling cascades. β-arrestin is known to trigger endocytosis and activation of the ERK pathway. In one example assay, bioluminescence resonance energy transfer or BRET has been used to study the interaction of GPCRs fused to *Renilla* luciferase (Rlu) with β-arrestin fused to green fluorescent protein (GFP). In this example, BRET is based on the transfer of energy between recombinant expressed GPCR-Rlu and β-arrestin-GFP when they are in close proximity after the addition of the luciferase substrate coelentcrazine, thus allowing measurement of real-time evaluation of these protein-protein interactions in whole cells.

Other assays have been developed, such as PathHunter® GPCR assays (DiscoveRx Corp., Fremont, Calif., USA) that directly measure GPCR activity by detecting β-arrestin interaction with the activated GPCR. Briefly, the GPCR is fused in frame with the small enzyme fragment ProLink™ and co-expressed in cells stably expressing a fusion protein of β-arrestin and a deletion mutant of β-galactosidase (i.e. β-gal, an enzyme acceptor, or EA). Activation of the GPCR stimulates binding of β-arrestin to the ProLink-tagged GPCR and the complementation of the two enzyme fragments results in formation of an active β-gal enzyme. An increase in enzyme activity (i.e. GPCR activation) can be measured using chemiluminescent detection reagents.

β-arrestin molecules have been shown to regulate GPCR internalization (i.e. endocytosis) following activation of GPCRs, such as APLNR. Agonist-activation of GPCRs leads to conformational changes, phosphorylation of the receptor, and activation of β-arrestin, or other pathways, to mediate receptor sequestration from the cell surface. The sequestration mechanism may be a means of desensitization (i.e. receptor is degraded following internalization) or resensitization (i.e. receptor is recycled back to the cell surface). See, e.g., Claing, A., et al. 2002, *Progress in Neurobiology* 66: 61-79, for review.

APLNR antagonists may block internalization of the receptor. APLNR agonists may induce internalization and/or resensitization of the APLNR (Lee, D K, et al. 2010, *BBRC*, 395:185-189). In some embodiments, the APLNR agonist exhibits or induces increased APLNR resensitization, as measured by an internalization assay. In other embodiments, the APLNR agonist exhibits or induces increased cell-surface receptor copy of the APLNR, as measured in an internalization assay. Measuring the extent (such as an increase) of receptor internalization in any internalization assay is done by determining the difference between the noninternalized measurement (i.e., cells without prior exposure to agonist) and the measurement obtained with agonist in the assay.

Apelin receptor sequestration, and thus apelin receptor copy, may be measured by a number of methods well-known in the art. APLNR agonist stimulation may result in increased or decreased receptor copy on the surface of a particular cell. For example, an apelin receptor agonist that induces APLNR internalization may have an effect on blood pressure. Receptor internalization assays are routinely done employing, for example, fluorescently-labeled or radiolabeled ligands, or immunofluorescent labels (fluorescently-tagged anti-receptor antibodies), followed by microscopy and digital imaging techniques (see, e.g., El Messari et al. 2004, *J Neurochem*, 90:1290-1301; and Evans, N., 2004, Methods of Measuring Internalization of G Protein-Coupled Receptors. *Current Protocols in Pharmacology*. 24: 12.6.1-12.6.22).

Phosphorylated ERK (p-ERK) may be measured in cell lysates from cells expressing APLNR receptors to determine APLNR activation. Endogenous extracellular signal-regulated kinase 1 and 2 (ERK1 and ERK2), belong to a conserved family of serine/threonine protein kinases and are involved cellular signaling events associated with a range of stimuli. The kinase activity of ERK proteins is regulated by dual phosphorylation at Threonine 202/Tyrosine 204 in ERK1, and Threonine 185/Tyrosine 187 in ERK2. MEK1 and MEK2 are the primary upstream kinases responsible for ERK 1/2 in this pathway. Many downstream targets of ERK 1/2 have been identified, including other kinases, and transcription factors. In one example, the p-ERK 1/2 assay utilizes an enzyme-linked immunosorbent assay (ELISA) method to measure specific phosphorylation of ERK 1 in cellular lysates of cell cultures expressing recombinant or endogenous receptors. In another example, the p-ERK 1/2 assay uses a primary (non-conjugated) antibody which recognizes phosphorylated Thr202/Tyr204 in ERK1 or phos-Thr185/Tyr187 in ERK2 and a secondary conjugated antibody that recognizes the primary antibody, whereas the secondary conjugated mAb provides a method of detection such as a conjugate reacts with an exogenously added substrate. Various commercial kits are available, such as AlphaScreen® SureFire™ (PerkinElmer), ThermoScientific (Waltham, Mass., USA), Sigma Aldrich (St. Louis, Mo., USA), ELISAOne (TGR BioSciences (South Australia, Australia) etc.).

As used herein, the term "binding", such as in the context of the binding of ligand to a receptor (e.g. GPCR), or such as an antibody binding to an antigen, typically refers to an interaction or association between a minimum of two entities, or molecular structures, such as a receptor-ligand interaction, or an antibody-antigen interaction. Thus a "receptor binding molecule" refers to a ligand or other moiety, such as a protein, that binds to, i.e. interacts with, a receptor.

For instance, binding affinity between the ligand (e.g., an apelin fusion protein) and the receptor (e.g., an APLNR or ligand binding fragment of APLNR) typically corresponds to a $K_D$ value of about $10^{-7}$ M or less, such as about $10^{-8}$ M or less, such as about $10^{-9}$ M or less. Binding affinity can be determined by any one or more of several methods, such as by surface plasmon resonance (SPR) using a BIAcore 3000 instrument. Accordingly, the ligand binds to the receptor with an affinity corresponding to a $K_D$ value that is at least ten-fold lower, such as at least 100 fold lower, for instance at least 1,000 fold lower, such as at least 10,000 fold lower, for instance at least 100,000 fold lower than its affinity for binding to a non-specific ligand (e.g., BSA, casein).

The term "$K_D$" (M), as used herein, refers to the dissociation equilibrium constant of a particular ligand-receptor interaction. There is an inverse relationship between $K_D$ and binding affinity, therefore the smaller the $K_D$ value, the higher the affinity. Thus, the term "lower affinity" relates to a lower ability to form an interaction and therefore a larger $K_D$ value.

The term "$k_d$" (sec$^{-1}$ or 1/s), as used herein, refers to the dissociation rate constant of a particular ligand-receptor interaction. Said value is also referred to as the $k_{off}$ value.

The term "$k_a$" (M$^{-1}$×sec$^{-1}$ or 1/M), as used herein, refers to the association rate constant of a particular ligand-receptor interaction.

The term "$K_A$" (M$^{-1}$ or 1/M), as used herein, refers to the association equilibrium constant of a particular ligand-receptor interaction, or the association equilibrium constant of antibody-antigen interaction. The association equilibrium constant is obtained by dividing the $k_a$ by the $k_d$.

The term "$EC_{50}$" or "EC50", as used herein, refers to the half maximal effective concentration, which includes the concentration of a ligand that induces a response, for example a cellular response, halfway between the baseline and maximum after a specified exposure time. The $EC_{50}$ essentially represents the concentration of a ligand where 50% of its maximal effect is observed. Thus, with regard to cellular signaling, increased activity is observed with a decreased $EC_{50}$ value, i.e. half maximal effective concentration value (less ligand needed to effect a greater response).

In one embodiment, decreased binding refers to an increased $EC_{50}$ protein concentration, which enables half-maximal binding to the target receptor or receptor-expressing cells.

In some embodiments, decreased activity refers to an increased $EC_{50}$ protein concentration, which enables half-maximal cellular activation of the target receptor or receptor-expressing cells.

The term "$IC_{50}$" or "IC50", as used herein, refers to the half maximal inhibitory concentration of a cellular response. In other words, the measure of the effectiveness of a particular moiety (e.g. protein, compound, or molecule) in inhibiting biological or biochemical function, wherein an assay quantitates the amount of such moiety needed to inhibit a given biological process. Thus, with regard to cellular signaling, a greater inhibitory activity is observed with a decreased $IC_{50}$, or half-maximal inhibitory concentration, value.

In one embodiment, the apelin fusion protein is an agonist of the APLNR with an EC50 of less than about 100 nM, or less than about 50 nM, or less than about 25 nM, or less than about 10 nM, or less than about 1 nM, in an in vitro assay that measures activation of the APLNR. In one embodiment, the apelin fusion protein comprises an Fc domain linked to the N-terminus of an apelin peptide, and exhibits an EC50 of less than about 1 nM, or less than about 500 ρM.

Apelin Fusion Proteins of the Invention

Methods of making fusion proteins are known in the art. In one such method, a DNA expression vector is engineered to contain an apelin-encoding nucleic acid sequence linked in-frame to an Fc-encoding nucleic acid sequence such that the DNA expression vector expresses one contiguous fusion polypeptide. Apelin peptide may be linked to the C-terminus or to the N-terminus of the Fc-containing polypeptide. Apelin fusion proteins of the invention are expected to be more stable than apelin peptides alone. Serum stable proteins include proteins that confer resistance to degradation or have a reduced clearance from the circulation. Exemplary serum stable apelin fusion proteins of the invention include SEQ ID NO: 2, SEQ ID NO: 4, SEQ ID NO: 39, SEQ ID NO: 40 and SEQ ID NO: 41.

In the context of constructing fusion proteins, the phrase "joined in-frame" means that the components are linked together is such a way that their complete translation, use or operation is possible and thus not disrupted. For example, a fusion protein comprising at least two polypeptides, may or may not have a linker or spacer sequence between the polypeptides, and thus the polypeptides are joined in-frame as one continuous polypeptide with each polypeptide maintaining its operability. Two or more polypeptides linked or fused together in a fusion protein are typically derived from two or more independent sources, and therefore a fusion protein comprises two or more linked polypeptides not normally found linked in nature. Furthermore, DNA encoding such fusion proteins may contain linker sequences that maintain operable in-frame (e.g. triplet codon) translation of the transcribed mRNA molecules encoding such polypeptides.

The phrase "operably linked", such as in the context of DNA expression vector constructs, a control sequence, e.g., a promoter or operator, is appropriately placed at a position relative to a coding sequence such that the control sequence directs the production of a polypeptide encoded by the coding sequence.

The term "signal peptide" or "signal peptide sequence" is defined herein as a peptide sequence usually present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed by enzyme cleavage. In some embodiments, said signal peptide may be capable of directing the polypeptide into a cell's secretory pathway. In some embodiments, the signal peptide comprises the amino acid sequence from 1-29 of mouse ROR1, GenBank Accession No. BAA75480 (SEQ ID NO: 10). In other embodiments the signal peptide has at least about 96%, or at least about 97%, or at least about 98%, or at least about 99% homology to the signal peptide amino acid sequence shown in SEQ ID NO: 9. In still other embodiments, the signal peptide is encoded by a nucleotide having at least about 96%, or at least about 97%, or at least about 98%, or at least about 99% homology to the signal peptide nucleic acid sequence shown in SEQ ID NO: 9.

In some embodiments, the components or peptides of an Fc-fusion protein are separated by a linker (or "spacer") peptide. Such peptide linkers are well known in the art (e.g., polyglycine) and typically allow for proper folding of one or both of the components of the fusion protein. The linker provides a flexible junction region of the component of the fusion protein, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part. Furthermore, the junction region should create an epitope that will not be recognized by the subject's immune system as foreign, in other words, will not be considered immunogenic. Linker selection may also have an effect on binding activity of the fusion molecule. (See Huston, et al, 1988, PNAS, 85:16: 5879-83; Robinson & Bates, 1998, *PNAS* 95(11):5929-34; Arai, et al. 2001, PEDS, 14(8):529-32; and Chen, X. et al., 2013, *Advanced Drug Delivery Reviews* 65:1357-1369.) In one embodiment, the apelin peptide is connected to the C-terminus or to the N-terminus of the Fc-containing polypeptide, or fragment thereof, via one or more peptide linkers.

The length of the linker chain may be 2, 3, 4, 5, 6, 7, 8, 9, 10, 11, 12, 13, 14 15 or more amino acid residues, but typically is between 5 and 25 residues. Examples of linkers include polyGlycine linkers, such as Gly-Gly, Gly-Gly-Gly (3Gly), 4Gly, 5Gly, 6Gly, 7Gly, 8Gly or 9Gly. Examples of linkers also include Gly-Ser peptide linkers such as Ser-Gly, Gly-Ser, Gly-Gly-Ser, Ser-Gly-Gly, Gly-Gly-Gly-Ser, Ser-Gly-Gly-Gly, Gly-Gly-Gly-Gly-Ser, Ser-Gly-Gly-Gly-Gly, Gly-Gly-Gly-Gly-Gly-Ser, Ser-Gly-Gly-Gly-Gly-Gly, Gly-Gly-Gly-Gly-Gly-Gly-Ser, Ser-Gly-Gly-Gly-Gly-Gly-Gly, (Gly-Gly-Gly-Gly-Ser)n, and (Ser-Gly-Gly-Gly-Gly)n, wherein n=1 to 10. (Gly-Gly-Gly-Gly-Ser)n and (Ser-Gly-Gly-Gly-Gly)n are also known as (G4S)n and (S4G)n, respectively.

In one such embodiment of the invention, the apelin peptide is connected to the C-terminus or to the N-terminus of the Fc-containing polypeptide, or fragment thereof, via one or more Gly-Ser peptide linkers.

In one embodiment, the peptide linker is (Gly-Gly-Gly-Gly-Ser)$_1$, (Gly-Gly-Gly-Gly-Ser)$_2$, (Gly-Gly-Gly-Gly-Ser)$_3$, or (Gly-Gly-Gly-Gly-Ser)$_4$. In one embodiment, the peptide linker comprises (Gly-Gly-Gly-Gly-Ser)$_3$ (SEQ ID NO: 11).

In some embodiments, the signal peptide is connected to the N-terminus of the Fc-fusion polypeptide via one or more peptide linkers or spacers. In some embodiments, the signal peptide is encoded upstream of the Fc-fusion protein in an expression vector and a spacer is encoded in-frame between the signal peptide and N-terminus of the Fc-fusion protein. In another embodiment, the peptide linker or spacer comprises RSTGSPGSG (SEQ ID NO: 12).

Modified Apelin Fusion Polypeptides

In other embodiments, the sequence of any Fc-fusion protein of the invention may be modified so that it does not comprise any acceptor sites for N-linked glycosylation. In still other embodiments, the sequence of any Fc-fusion protein of the invention may be modified to enhance or diminish antibody binding to the FcRn receptor, e.g., at acidic pH as compared to neutral pH. In other embodiments, the sequence of any Fc-fusion protein of the invention may be modified to resist cleavage or degradation. As such, addition of one or more C-terminal amino acids to the apelin peptide of an apelin-Fc-fusion protein may confer increased stability, such as resistance to degradation. Without being bound by one theory, additional C-terminal amino acids may eliminate susceptibility to cleavage sites within the peptide or fusion protein. Stability may be conferred due to decreased or slowed clearance from the circulation (i.e. renal excretion or clearance). Such modifications to apelin peptides do not alter their ability to activate the APLNR. Exemplary modified apelin peptides are included in Tables 3 and 4, e.g. SEQ ID NO: 38, SEQ ID NO: 42, SEQ ID NO: 43, and SEQ ID NO: 44. Exemplary apelin fusion proteins of the invention include SEQ ID NO: 39, SEQ ID NO: 40 and SEQ ID NO: 41.

In general, proteins, including Fc-fusion proteins described herein may be modified by inclusion of any suitable number of such modified amino acids (including non-standard amino acids, discussed supra) and/or associations with conjugated substituents. Suitability in this context is generally determined by the ability to at least substantially retain the Fc-fusion protein's associated selectivity and/or specificity, for example binding to APLNR. The modified amino acid may, for instance, be selected from a glycosylated amino acid, a PEGylated amino acid, a farnesylated amino acid, a geranyl-geranylated amino acid, an acetylated amino acid, a biotinylated amino acid, an amino acid conjugated to a lipid moiety, or an amino acid conjugated to an organic derivatizing agent, or the like. The inclusion of one or more modified amino acids may be advantageous in, for example, further increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means. Non-limiting examples of a modified amino acid include a glycosylated amino acid, a sulfated amino acid, a prenylated (e.g., farnesylated, geranyl-geranylated) amino acid, an acetylated amino acid, an acylated amino acid, a fatty acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker, 1998, Protein Protocols On CD-Rom, Humana Press, Totowa, N.J.

Proteins, including Fc-fusion proteins of the invention may also be chemically modified by covalent conjugation to a polymer to, for instance, further increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol). See, e.g., WO2012/125408, which describes a PEG-apelin-36, a polypeptide with prolonged inotropic effects in rats.

In one embodiment, proteins including Fc-fusion proteins comprising one or more radiolabeled amino acids are provided. A radiolabeled antibody may be used for both diagnostic and therapeutic purposes. In another embodiment, proteins, including Fc-fusion proteins of the present invention may be conjugated to a molecule which is a therapeutic agent or a detectable marker. In one embodiment, the therapeutic agent is a cytotoxic agent, such as a radioisotope. Examples of radioisotopes for polypeptides include, but are not limited to, $^3$H, $^{14}$C, $^{15}$N, $^{35}$S, $^{90}$Y, $^{99}$Tc, and $^{125}$I, $^{131}$I, $^{186}$Re, and $^{225}$AC. Methods for preparing radiolabeled amino acids and related peptide derivatives are known in the art (see for instance Junghans et al., in *Cancer Chemotherapy and Biotherapy* 655-686 (2nd edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (U.S. RE35,500), U.S. Pat. No. 5,648,471 and U.S. Pat. No. 5,697,902. For example, a radioisotope may be conjugated by a chloramine T method. In further embodiments, a detectable marker may be a radiolabel, an enzyme, a chromophore, or a fluorescent label.

Expression Systems

The invention provides an expression vector encoding a polypeptide, e.g. an apelin Fc-fusion protein of the invention. Such expression vectors may be used for recombinant production of polypeptides of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an Fc-fusion protein or polypeptide-encoding nucleic acid molecule is comprised in a naked DNA or RNA vector, including, for example, a linear expression element (as described in, for instance, Sykes and Johnston, *Nat Biotech* 12, 355-59 (1997)), a compacted nucleic acid vector (as described in for instance U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. No. 5,589,466 and U.S. Pat. No. 5,973,972).

In another embodiment, the vector comprises a nucleic acid molecule encoding a polypeptide of the invention, including an expression vector comprising the nucleic acid molecules described wherein the nucleic acid molecule is operatively linked to an expression control sequence.

In one embodiment, the vector is suitable for expression of a polypeptide of the invention in a bacterial cell. Examples of such vectors include expression vectors such as BlueScript (Stratagene), pIN vectors (Van Heeke & Schuster, 1989, *J Biol Chem* 264, 5503-5509), pET vectors (Novagen, Madison, Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed., 1987, Current Protocols in Molecular Biology, Greene Publishing and Wiley InterScience New York; and Grant et al., 1987, *Methods in Enzymol* 153, 516-544).

In other embodiments, the expression vector is suitable for expression in baculovirus-infected insect cells. (Kost, T; and Condreay, J P, 1999, *Current Opinion in Biotechnology* 10 (5): 428-33.)

A vector comprising a nucleic acid molecule of the invention is provided, wherein the nucleic acid molecule is operably linked to an expression control sequence suitable for expression in a mammalian host cell.

Expression control sequences are engineered to control and drive the transcription of genes of interest, and subsequent expression of proteins in various cell systems. Plasmids combine an expressible gene of interest with expression control sequences (i.e. expression cassettes) that comprise desirable elements such as, for example, promoters, enhancers, selectable markers, operators, etc. In an expression vector of the invention, Fc-fusion protein or antibody-encoding nucleic acid molecules may comprise or be associated with any suitable promoter, enhancer, selectable marker, operator, repressor protein, polyA termination sequences and other expression-facilitating elements.

"Promoter" as used herein indicates a DNA sequence sufficient to direct transcription of a DNA sequence to which it is operably linked, i.e., linked in such a way as to permit transcription of the Fc-fusion protein or antibody-encoding nucleotide sequence when the appropriate signals are present. The expression of a Fc-fusion protein or antibody-encoding nucleotide sequence may be placed under control of any promoter or enhancer element known in the art. Examples of such elements include strong expression promoters (e.g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters).

In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules of the invention may also be operably linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a fluorescent protein marker are made visible, and are thus selectable. Embodiments include beta-lactamase (bla) (beta-lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene).

In certain embodiments, the vector comprises one or more selectable marker genes selected from the group consisting of bla, bls, BSD, bsr, Sh ble, hpt, tetR, tetM, npt, kanR and pac. In other embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), or yellow fluorescent protein (YFP).

For the purposes of this invention, gene expression in eukaryotic cells may be tightly regulated using a strong promoter that is controlled by an operator that is in turn regulated by a regulatory protein, which may be a recombinant "regulatory fusion protein" (RFP). The RFP consists essentially of a transcription blocking domain, and a ligand-binding domain that regulates its activity. Examples of such expression systems are described in US20090162901A1, which is herein incorporated by reference in its entirety.

As used herein "operator" indicates a DNA sequence that is introduced in or near a gene in such a way that the gene may be regulated by the binding of the RFP to the operator and, as a result, prevents or allow transcription of the gene of interest, i.e. a nucleotide encoding a polypeptide of the invention. A number of operators in prokaryotic cells and bacteriophage have been well characterized (Neidhardt, ed., *Escherichia coli* and *Salmonella*; Cellular and Molecular Biology 2d. Vol 2 ASM Press, Washington D.C. 1996). These include, but are not limited to, the operator region of the LexA gene of *E. coli*, which binds the LexA peptide, and the lactose and tryptophan operators, which bind the repressor proteins encoded by the LacI and trpR genes of *E. coli*. These also include the bacteriophage operators from the lambda $P_R$ and the phage P22 ant/mnt genes, which bind the repressor proteins encoded by lambda cI and P22 arc. In some embodiments, when the transcription blocking domain of the RFP is a restriction enzyme, such as NotI, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

In certain embodiments, the operator is selected from the group consisting of tet operator (tetO), NotI recognition sequence (not familiar with this; I know NotI as a restriction enzyme), LexA operator, lactose operator, tryptophan operator and Arc operator (AO). In some embodiments, the repressor protein is selected from the group consisting of TetR, LexA, LacI, TrpR, Arc, LambdaC1 and GAL4. In other embodiments, the transcription blocking domain is derived from a eukaryotic repressor protein, e.g. a repressor domain derived from GAL4. Bacterial operators can be employed in mammalian and other host cell systems (see, e.g., US 20090162901A1, which is herein incorporated by reference).

In an exemplary cell expression system, cells are engineered to express the tetracycline repressor protein (TetR) and a protein of interest is placed under transcriptional control of a promoter whose activity is regulated by TetR. Two tandem TetR operators (tetO) are placed immediately downstream of a CMV-MIE promoter/enhancer in the vector. Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription then translation (expression) of the protein of interest occurs. (See, e.g., U.S. Pat. No. 7,435,553, which is herein incorporated by reference in its entirety.)

Another exemplary cell expression system includes regulatory fusion proteins such as TetR-$ER_{LBD}$T2 fusion protein, in which the transcription blocking domain of the fusion protein is TetR and the ligand-binding domain is the estrogen receptor ligand-binding domain ($ER_{LBD}$) with T2 mutations ($ER_{LBD}$T2; Feil et al., 1997, *Biochem. Biophys. Res. Commun.* 237:752-757). When tetO sequences were placed downstream and proximal to the strong CMV-MIE promoter, transcription of the nucleotide sequence of interest from the CMV-MIE/tetO promoter was blocked in the presence of tamoxifen and unblocked by removal of tamoxifen. In another example, use of the fusion protein Arc2-$ER_{LBD}$T2, a fusion protein consisting of a single chain dimer consisting of two Arc proteins connected by a 15 amino acid linker and the $ER_{LBD}$T2 (supra), involves an Arc operator (AO), more specifically two tandem arc operators immediately downstream of the CMV-MIE promoter/enhancer. Cell lines may be regulated by Arc2-$ER_{LBD}$T2, wherein cells expressing the protein of interest are driven by a CMV-MIE/ArcO2 promoter and are inducible with the removal of tamoxifen. (See, e.g., US 20090162901A1, which is herein incorporated by reference.)

In some embodiments, a vector of the invention comprises a CMV-MIE/TetO or CMV-MIE/AO2 hybrid promoter.

The vectors of the invention may also employ Cre-lox recombination tools to facilitate the integration of a gene of interest into a host genome. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. (See, e.g. Araki et al., 1995, *PNAS* 92:160-4; Nagy, A. et al., 2000, *Genesis* 26:99-109; Araki et al., 2002, *Nuc Acids Res* 30(19): e103; and US20100291626A1, all of which are herein incorporated by reference). In another recombination strategy, yeast-derived FLP recombinase may be utilized with the consensus sequence FRT (see also, e.g. Dymecki, S. M., 1996, *PNAS* 93(12): 6191-6196).

In another aspect, a gene (i.e. a nucleotide sequence encoding a recombinant polypeptide of the invention) is inserted within an expression-enhancing sequence of the expression cassette, and is optionally operably linked to a promoter, wherein the promoter-linked gene is flanked 5' by a first recombinase recognition site and 3' by a second recombinase recognition site. Such recombinase recognition sites allow Cre-mediated recombination in the host cell of the expression system. In some instances, a second promoter-linked gene is downstream (3') of the first gene and is flanked 3' by the second recombinase recognition site. In still other instances, a second promoter-linked gene is flanked 5' by the second recombinase site, and flanked 3' by a third recombinase recognition site. In some embodiments, the recombinase recognition sites are selected from a loxP site, a lox511 site, a lox2272 site, and a FRT site. In other embodiments, the recombinase recognition sites are different. In a further embodiment, the host cell comprises a gene capable of expressing a Cre recombinase.

In some embodiments, the vector further comprises an X-box-binding-protein 1 (mXBP1) gene capable of enhancing protein production/protein secretion through control of the expression of genes involved in protein folding in the endoplasmic reticulum (ER). (See, e.g. Ron D, and Walter P., 2007, *Nat Rev Mol Cell Biol.* 8:519-529).

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g. *S. cerevisiae, S. pombe, P. partoris, P. methanolica*, etc.), plant cells, insect cells (e.g. SF-9, SF-21, baculovirus-infected insect cells, *Trichoplusia ni*, etc.), non-human animal cells, mammalian cells, human cells, or cell fusions such as, for example, hybridomas or quadromas. In certain embodiments, the cell is a human, monkey, ape, hamster, rat or mouse cell. In other embodiments, the cell is eukaryotic and is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g. a PER.C6® cell).

In some embodiments, the cell is a CHO cell. In other embodiments, the cell is a CHO K1 cell.

For example, in one embodiment, the present invention provides a host cell comprising a nucleic acid stably integrated into the cellular genome that comprises a nucleotide sequence coding for expression of a recombinant polypeptide of the present invention. In another embodiment, the present invention provides a cell comprising a non-integrated (i.e., episomal) nucleic acid, such as a plasmid, cosmid, phagemid, or linear expression element, which comprises a sequence coding for expression of a recombinant polypeptide of the invention. In other embodiments, the present invention provides a cell line produced by stably transfecting a host cell with a plasmid comprising an expression vector of the invention.

In a further aspect, the invention relates to a method for producing an Fc-fusion protein of the invention, said method comprising the steps of a) culturing a host cell of the invention as described herein above, and b) purifying the Fc-fusion protein (supra) from the culture media.

Therapeutic and Diagnostic Uses of the Invention

In an even further aspect, the invention relates to a composition comprising an apelin fusion polypeptide or protein as defined herein.

The compositions may be formulated with pharmaceutically acceptable carriers or diluents as well as known adjuvants and excipients in accordance with conventional techniques such as those disclosed in Remington: The Science and Practice of Pharmacy, 19th Edition, Gennaro, Ed., Mack Publishing Co., Easton, Pa., 1995, and using trial and error experimentation.

The pharmaceutically acceptable carriers or diluents as well as any other known adjuvants and excipients should be suitable for the chosen apelin fusion or apelin Fc-fusion protein of the present invention and the chosen mode of administration. The actual dosage levels of the active ingredients in the pharmaceutical compositions of the present invention may be varied so as to obtain an amount of the active ingredient which is effective to achieve the appropriate stability of drug substance, desired therapeutic response for a particular patient, composition, and mode of administration. The selected dosage level will depend upon a variety of pharmacokinetic factors.

The pharmaceutical composition may be administered by any suitable route and mode. Suitable routes of administering an apelin fusion protein of the present invention in vivo are well known in the art and may be selected by those of ordinary skill in the art. (Daugherty, A L, and Msrny, R J, 2006, *Adv Drug Delivery Rev,* 58(5-6): 686-706).

Apelin fusion proteins are agents administered for the management of cardiovascular conditions, such as inotropic agents, specifically positive inotropic agents. Without being bound to a particular theory, positive inotropic agents increase myocardial contractility, and are used to support cardiac function in conditions such as congestive heart failure, myocardial infarction, cardiomyopathy, and others. (See Dai, et al., 2006, *Eur J Pharmacol* 553(1-3): 222-228; Maguire, et al, *Hypertension.* 2009; 54:598-604; and Berry, M., et al., 2004 *Circulation,* 110:11187-11193.) Apelin-induced vasodilation may be protective in ischemia-reperfusion injury. Promotion of angiogenesis and induction of larger nonleaky vessels by apelin peptides may contribute to functional recovery from ischemia. (Eyries M, et al., 2008, *Circ Res* 103:432-440; Kidoya H, et al., 2010, *Blood* 115:3166-3174).

Apelin receptor agonists are considered pro-angiogenic agents which are administered to increase cardiac output, improve cardiac function, stabilize cardiac function, limit a decrease in cardiac function, or promote new blood vessel growth in an ischemic or damaged area of the heart or other tissue. Thus, apelin receptor agonists of the invention are useful to promote angiogenesis and therefore treat ischemia, restore bloodflow to ischemic organs and tissues, for example to treat limb ischemia, peripheral ischemia, renal ischemia, ocular ischemia, cerebral ischemia, or any ischemic disease.

Apelin fusion proteins of the invention are agents administered to increase blood flow, or increase heart contractility, such as to treat or alleviate ischemia and heart failure.

Apelin fusion proteins are agents administered to treat or alleviate ischemia and reperfusion injury, such as to limit ischemia/reperfusion (I/R) injury or delay the onset of necrosis of the heart tissue, or to provide preventive treatment, for example, to protect the heart from ischemia/reperfusion (I/R) injury, improve cardiac function, or limit the development myocardial infarction.

Apelin fusion proteins are agents administered for the management of metabolic conditions related to diabetes and obesity. Apelin improves glucose tolerance and enhances glucose utilization, by muscle tissue, in obese insulin-resistant mice (Dray et al., 2008, *Cell Metab* 8:437-445). Apelin KO mice have diminished insulin sensitivity (Yue at al., 2010, *Am J Physiol Endocrinol Metab* 298:E59-E67). As such, Apelin fusion proteins are agents administered to improve glucose-tolerance in the treatment of insulin-resistant diabetes.

Changes in muscle apelin mRNA levels are also correlative with whole-body insulin sensitivity improvements (Besse-Patin, A. et al., 2013 Aug. 27, *Int J Obes (Lond).* doi: 10.1038/ijo.2013.158, Epub ahead of print). Due to such metabolic improvements in muscle tissue, and apelin-induced vasodilation, agonistic apelin fusion proteins may also be administered to stimulate muscle growth and endurance.

It has been shown that primary HIV-1 isolates can also use APLNR as a coreceptor and synthetic apelin peptides inhibited HIV-1 entry into CD4-APLNR-expressing cells (Cayabyab, M., et al., 2000, *J. Virol.,* 74: 11972-11976). Apelin fusion proteins are administered to treat HIV infection.

Apelin-neuroprotection is also seen where apelin peptides act through signaling pathways to promote neuronal survival (Cheng, B, et al., 2012, *Peptides,* 37(1):171-3). Apelin fusion proteins are administered to promote or increase survival of neurons.

An apelin receptor agonist is also described as a hot flash suppressant. (See WO2012/133825, published Oct. 4, 2012.) Apelin fusion proteins of the invention may also be administered to treat, improve or suppress hot flash symptoms in a subject.

Apelin peptide may promote obesity through adipose tissue expansion. Apelin is induced by hypoxia and drives angiogenesis within the hypoxic interior of expanding adipose tissue. (Kunduzova O, et al., 2008, *FASEB J,* 22:4146-4153). Some apelin fusion proteins however are antagonists of the APLNR that act as inhibiting agents of this mechanism, in a tissue-specific manner, to promote weight loss or treat obesity. Therefore, apelin fusion proteins are blocking agents administered to treat obesity and to promote weight loss.

Pathological angiogenesis, involved in promoting tumor growth or neovascularization in the retina may be responsive to apelin or APLNR antagonist. (Kojima, Y. and Quertermous, T., 2008, *Arterioscler Thromb Vasc Biol,* 28:1687-1688; Rayalam, S. et al. 2011, *Recent Pat Anticancer Drug Discov* 6(3):367-72). As such, apelin fusion proteins are inhibiting agents administered to slow tumor growth or metastasis, or to treat cancer and metastatic disease. Apelin fusion proteins are also administered to treat retinopathy.

APLNR antagonists may also reduce angiogenesis and improve function, such as in fibrotic tissues, by ameliorating the effects of an overactive apelin system caused by a pathogenic disease (Principe, et al., 2008; Reichenbach, et al., 2012, *JPET* 340(3):629-637). Without being bound by any one theory, blocking the apelin system may slow the formation of excess fibrous connective tissue in an organ or tissue in a reparative or reactive process, such as in a pathological condition like cirrhosis. As such, apelin fusion proteins may be used as inhibiting agents administered to slow or prevent the progression of fibrosis, or to treat fibrosis.

In some embodiments, Fc-fusion proteins of the invention provide a method for the treatment of a disease or condition, the method comprising administering to a subject in need thereof a therapeutically effective amount of an apelin fusion protein sufficient to treat the disease or condition.

In one embodiment, provided herein is a method for treatment of a disease or condition related to apelin in a subject in need thereof, the method comprising administering to the subject a therapeutically effective amount of an apelin fusion protein.

In some embodiments, the apelin fusion protein comprises a polypeptide comprising an apelin peptide fused to an Fc domain, or a fragment thereof.

Diseases or conditions are selected from the group consisting of cardiovascular disease, acute decompensated heart failure, congestive heart failure, myocardial infarction, cardiomyopathy, ischemia, ischemia/reperfusion injury, pulmonary hypertension, diabetes, obesity, cancer, metastatic disease, fluid homeostasis, pathological angiogenesis, retinopathy, and HIV infection.

In some embodiments, the apelin fusion protein is an APLNR agonist useful for treating a disease or condition selected from the group consisting of cardiovascular disease, acute decompensated heart failure, congestive heart failure, myocardial infarction, cardiomyopathy, ischemia, ischemia/reperfusion injury, pulmonary hypertension, diabetes, hot flash symptoms, fluid homeostasis, and HIV infection. In another embodiment, the apelin fusion protein is an APLNR agonist that promotes neuronal cell survival. In another embodiment, the apelin fusion protein is an APLNR agonist that decreases sensitivity to insulin.

In some embodiments, the apelin fusion protein is an APLNR antagonist useful for treating a disease or condition selected from the group consisting of obesity, cancer, metastatic disease, retinopathy, fibrosis, and pathological angiogenesis. In one embodiment, the apelin fusion protein is an APLNR antagonist that promotes weight loss. In one embodiment, the apelin fusion protein is an APLNR antagonist that decreases pathological angiogenesis or neovascularization. In other embodiments, the apelin fusion protein is an APLNR antagonist that decreases or inhibits tumor growth.

As used herein, a "therapeutically effective amount" of an Fc-fusion protein means an amount sufficient to ameliorate, alleviate or partially arrest the clinical manifestations of a given disease and its complications in a therapeutic intervention comprising the administration of said protein. An amount adequate to accomplish this is defined as "therapeutically effective amount". Effective amounts for each purpose will depend on the severity of the disease or injury as well as the weight and general state of the subject.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active ingredient (Fc-fusion protein) to alleviate or relieve symptoms and/or complications, to delay the progression of the disease, disorder or condition, and/or to remedy or eliminate the disease, disorder or condition as well as to prevent the condition, wherein prevention is to be understood as the management and care of a patient for the purpose of stopping the disease progression, and includes the administration of the active ingredients to prevent the onset of the symptoms or complications. Nonetheless, preventive, palliative, and therapeutic (curative) treatments are each aspects of the invention. The subject to be treated is a mammal, in particular a human being.

In some embodiments, the treatment is maintenance treatment, recurrence prevention or stabilization of the disease or condition.

The present invention includes compositions and therapeutic formulations comprising any of the apelin fusion proteins described herein in combination with one or more additional therapeutically active components, and methods of treatment comprising administering such combinations to subjects in need thereof.

Such additional therapeutically active components include VEGF inhibitors, blood pressure medication, calcium channel blockers, digitalis, anti-arrhythmics, ACE inhibitors, anti-coagulants, immunosuppressants, pain relievers, vasodilators, etc.

The apelin fusion proteins of the invention provide agents with improved pharmacokinetic properties, such as circulating serum half-life and stability compared to apelin peptides that do not have an Fc domain or fragment of an Fc domain. In one embodiment, the apelin fusion protein post-injection serum level is increased or elevated for more than about 1 hour, or more than about 2 hours, or more than about 3 hours, or more than about 4 hours, or more than about 5 hours, or more than about 10 hours, or more than about 24 hours. In other embodiments, the apelin fusion protein has a serum or plasma half-life of more than about 10 minutes, or more than about 1 hour, or more than about 2, 3, 4, 5, 6, 7, 8, 9, or more than about 10 hours, or more than about 24 hours.

Labeled apelin fusion proteins of the invention can be used for diagnostic purposes to detect, diagnose, or monitor diseases or disorders. The invention provides for the detection or diagnosis of a disease or disorder, comprising: (a) assaying the existence of apelin receptor (APLNR) in cells or tissue samples of a subject using one or more apelin fusion proteins that immunospecifically bind to the target APLNR; and (b) comparing the level of the APLNR with a control level, e.g. levels in normal tissue samples, whereby an increase in the assayed level of APLNR compared to the control level of APLNR is indicative of the disease or disorder, or indicative of the severity of the disease or disorder.

Apelin fusion proteins of the invention can be used to assay APLNR levels in a biological sample using immunohistochemical methods well-known in the art. Other apelin-based methods useful for detecting APLNR protein include immunoassays such as the enzyme linked immunoassay (ELISA) and the radioimmunoassay (RIA). Suitable apelin fusion protein labels may be used in such kits and methods, and labels known in the art include enzyme labels, such as alkaline phophatase and glucose oxidase; radioisotope labels, such as iodine ($^{125}$I, $^{131}$I) carbon ($^{14}$C), sulfur ($^{35}$S), tritium ($^{3}$H), indium ($^{121}$In), and technetium ($^{99m}$Tc); and luminescent labels, such as luminol and luciferase; and fluorescent labels, such as fluorescein and rhodamine.

Presence of labeled apelin fusion proteins may be detected in vivo for diagnosis purposes. In one embodiment, diagnosis comprises: a) administering to a subject an effective amount of a labeled apelin fusion proteins; b) waiting for a time interval following administration for permitting labeled apelin fusion protein to concentrate at sites where APLNR may be detected and to allow for unbound labeled apelin fusion protein to be cleared to background level; c) determining a background level; and d) detecting the labeled apelin fusion protein in the subject, such that detection of labeled apelin fusion protein above the background level is indicative that the subject has increased APLNR protein, or has the disease or disorder, or the increase APLNR protein is indicative of the severity of the disease or disorder. In accordance with such embodiment, the apelin fusion protein is labeled with an imaging moiety suitable for detection using a particular imaging system known to those skilled in the art. Background levels may be determined by various methods known in the art, including comparing the amount of labeled apelin fusion protein detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

The invention also provides a pack or kit (e.g., a pharmaceutical pack or kit) comprising one or more containers filled with at least one activating fusion protein of the invention. The kits of the invention may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or (c) both approval for manufacture and directions for use.

Ex Vivo and In Vivo Assays

Apelin Fc-fusion proteins of the invention maintain substantial activity with respect to the APLNR while prolonging serum half-life. APLNR signal transduction provides the nexus between apelin Fc-fusion proteins and the known therapeutic and biological effects of apelin. Therefore, any demonstration of an apelin Fc-fusion protein effect on APLNR activity in vitro, ex vivo, or in vivo provides reasonable evidence of an in vivo biological or medical effect of the apelin Fc-fusion protein in a patient or animal. Among other studies, it has been demonstrated that apelin/APLNR is an endogenous protective system against myocardial ischemia/reperfusion (I/R) injury and the anti-apoptotic effects of apelin/APLNR activation, specifically pERK, protects against such injury (Zeng, et al. 2009, *Peptides,* 30(6):1144-52, epub Feb. 24, 2009).

Agonists of APLNR, including endogenous apelin peptides, apelin analogues, and modified apelin peptides, demonstrate therapeutic activity in a number of in vivo assays (e.g. PEG-apelin-36, as in WO2012125408, and non-peptidic apelin agonists as in Iturrioz, X. et al. 2010, *FASEB J,* 24(5): 1506-17. Epub Dec. 29, 2009).

APLNR agonism has been demonstrated to result in increased heart rate and cardiac contractility (Ashley, E A, et. al. 2005, *Cardiovasc Res.* 65(1):73-82). In addition, apelin peptide has been demonstrated to alter the electrophysiology of cardiomyocytes. Whole-cell patch-clamp techniques were used to investigate the action potential (AP) and ionic currents in isolated rabbit left atrial (LA) myocytes before and after the administration of apelin (See, e.g., Farkasfalvi, K., et al., 2007, *Biochem Biophys Res Commun.* 357(4):889-95. Epub 2007 Apr. 12; and Cheng, C C, et al., 2013, *Eur J Clin Invest.* 43(1):34-40. Epub Oct. 28, 2012; which are both incorporated by reference herein). Isotropy induced by apelin agonism may also be assessed by measuring ECG parameters in isolated hearts from mice or rats using a Langendorf or Working Heart System. Such electrophysiological and in vivo techniques, such as micro-ultrasound or echocardiography, are used to assess the therapeutic action of the polypeptides of the invention.

The protective effects of apelin Fc-fusion polypeptides may be assessed following myocardial ischemia/reperfusion (I/R) injury or hypoxia/re-oxygenation (H/R) in isolated rat or mouse hearts as in the Langendorf system (see e.g. Zeng, et al. 2009, *Peptides,* 30(6):1144-52, epub Feb. 24, 2009; Pisarenko, et al. 2010, *Kardiologiia,* 50(10):44-9; and Pisarenko, et al., 2013, *J Pharmacol Pharmacother*. "Effects of structural analogues of apelin-12 in acute myocardial infarction in rats", epub before print).

Transient LAD ligation may also be performed, with apelin agonist administered prior to reperfusion. (See Pisarenko, et al. 2011, *Bull Exp Biol Med.* 152(1):79-82; Li, L. et al, 2012, *Am J Physiol Heart Circ Physiol,* 303(5):H605-18, Epub Jun. 29, 2012; and Tao, J., et al, 2011, *Am J Physiol Heart Circ Physiol,* 301(4):H1471-86, Epub Jul. 29, 2011.) Following cardiac injury, microultrasound parameters may be used to measure cardiac function with respect to improvement, as well as assessment of infarct size.

The following examples are provided to describe to those of ordinary skill in the art how to make and use methods and compositions of the invention, and are not intended to limit the scope of what the inventors regard as their invention. Efforts have been made to ensure the accuracy with respect to numbers used (e.g. amounts, concentrations, temperature, etc.) but some experimental errors and deviations should be accounted for.

EXAMPLES

Example 1

Cloning of Expression Constructs

Figure 3B:
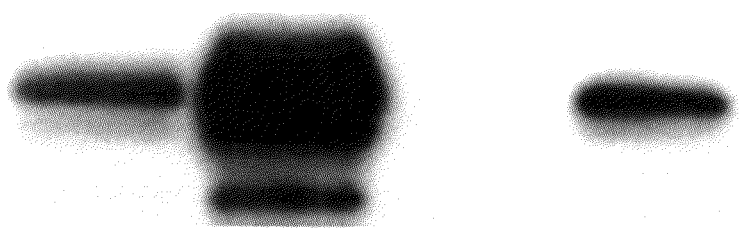
FIG. 3B illustrates the reactivity of either 10 ng or 100 ng of isolated hFc-apelin13 or apelin13-hFc protein in a Western blot with anti-apelin antibody.

Synthetic gene fragments were used to generate N-terminal and C-terminal hFc fusions with apelin-13. DNA encoding the resulting fusions, hFc-Apelin13 (SEQ ID NO: 1) and Apelin13-hFc (SEQ ID NO: 3), were inserted into expression vectors downstream of a CMV promoter, using standard molecular cloning techniques. CHO stable cell lines were generated and used for the production of fusion proteins, which were then purified by affinity methods. N-terminal hFc-Apelin13 and C-terminal Apelin13-hFc fusion proteins migrate on SDS-PAGE gels consistent with their predicted mass. (See FIG. 3A.) Western blot analysis, performed with the anti-apelin antibody (Abcam, #ab59469), was used to confirm presence of apelin on hFc-Apelin13 and Apelin13-hFc. (See FIG. 3B.)

Example 2

Potency and Efficacy of Apelin Fc Fusion Proteins in a cAMP-Reporter Assay

Modulation of intraceullular cAMP levels by unmodified apelin peptide (Bachem, #H-4568.0001) and apelin 13 fusion proteins of the invention was evaluated using a bioassay that was developed to detect the activation of hAPLNR. A HEK293 cell line was transfected to stably express the full-length human hAPLNR (amino acids 1-380 of accession number NP_005152.1), along with a luciferase reporter [cAMP response element (CRE,4×)-luciferase]. The resulting cell line, HEK293/CRE-luc/hAPLNR, was maintained in DMEM containing 10% FBS, NEAA, pencillin/streptomycin, and 100 µg/mL hygromycin B. For the bioassay, HEK293/CRE-luc/hAPLNR cells were seeded onto 96-well assay plates at 20,000 cells/well in 80 µL of OPTIMEM supplemented with 0.1% FBS and penicillin/streptomycin/L-glutamine and incubated for 16 hours at 37° C. in 5% $CO_2$. The next morning, to measure inhibition of forskolin-induced cAMP production via hAPLNR activation, unmodified apelin peptide and apelin 13 fusion proteins were serially diluted (1:3) then mixed with forskolin (Sigma, # F6886) in assay buffer (5 µM final forskolin concentration), and added to the cells. After 5 hours of incubation at 37° C. in 5% $CO_2$, luminescence was measured following the addition of One Glo reagent (Promega, #E6051) using a Victor X instrument (Perkin Elmer). The data were fit by nonlinear regression to a 4-parameter logistic equation with Prism 5 software (Graph Pad).

Figure 4:
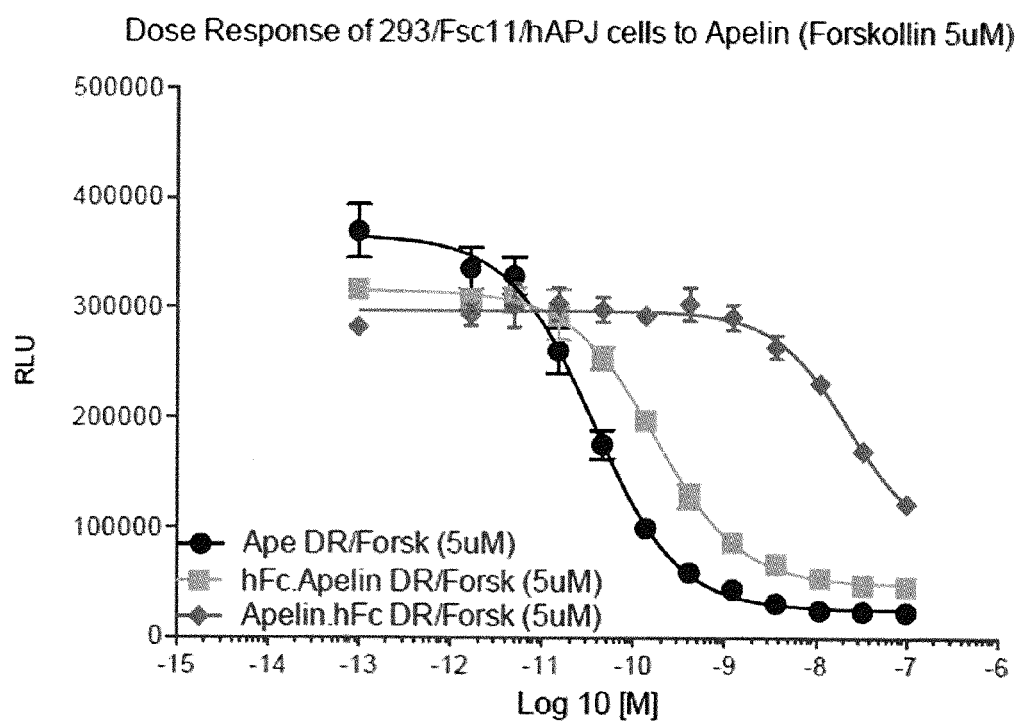
FIG. 4 represents the dose-response curve and half-maximal concentrations (EC50s) of each of the following ligands: apelin-13 (-●-), hFc-apelin13 (-■-), or apelin13-hFc (-♦-) in a CRE-luc assay by measuring forskolin-induced cAMP response in APJ (APNLR)-expressing cells.

The hFc-Apelin13 fusion protein promoted inhibition of cAMP release from forskolin-stimulated HEK293/CRE-luc/hAPLNR cells with an $EC_{50}$ value of 174 pM and Apelin13-hFc activated with an $EC_{50}$ value of 22.1 nM. In this assay, apelin-13 activated with an $EC_{50}$ value of 36.5 pM. (See FIG. 4.)

Example 3

Potency and Efficacy of Fc Fusion Proteins in a β-Arrestin Assay

The DiscoverX PathHunter® platform is based on the recruitment of β-arrestin to GPCRs in response to treatment with a relevant ligand. In this assay format, β-arrestin is fused to an N-terminal deletion mutant of β-galactosidase (β-gal) and stably-expressed in the cells whereas the GPCR is fused to a smaller (42 amino acids), weakly complementing β-gal fragment. Ligand stimulation of the GPCR in this assay results in the recruitment of β-arrestin to the GPCR, forcing the complementation of the two β-gal fragments and resulting in the formation of a functional enzyme that converts substrate to detectable signal (DiscoverX Corporation, Fremont, Calif., USA).

For the assay, CHO-K1/hAPLNR DiscoverX cells were plated at 10,000 cells per well in assay media (DiscoverX Corporation; #93-0250E2) and incubated for 48 hours at 37° C. in 5% $CO_2$. Cells were then treated with a 1:10 serial dilution of either unmodified apelin-13 peptide or the apelin-13 fusion proteins. After 1.5 hours of incubation at 37° C., detection reagents were added as per the manufacturer's specifications and incubated for 1 hour at RT, followed by luminescence measurement using a Victor instrument (Perkin-Elmer)

Figure 5:
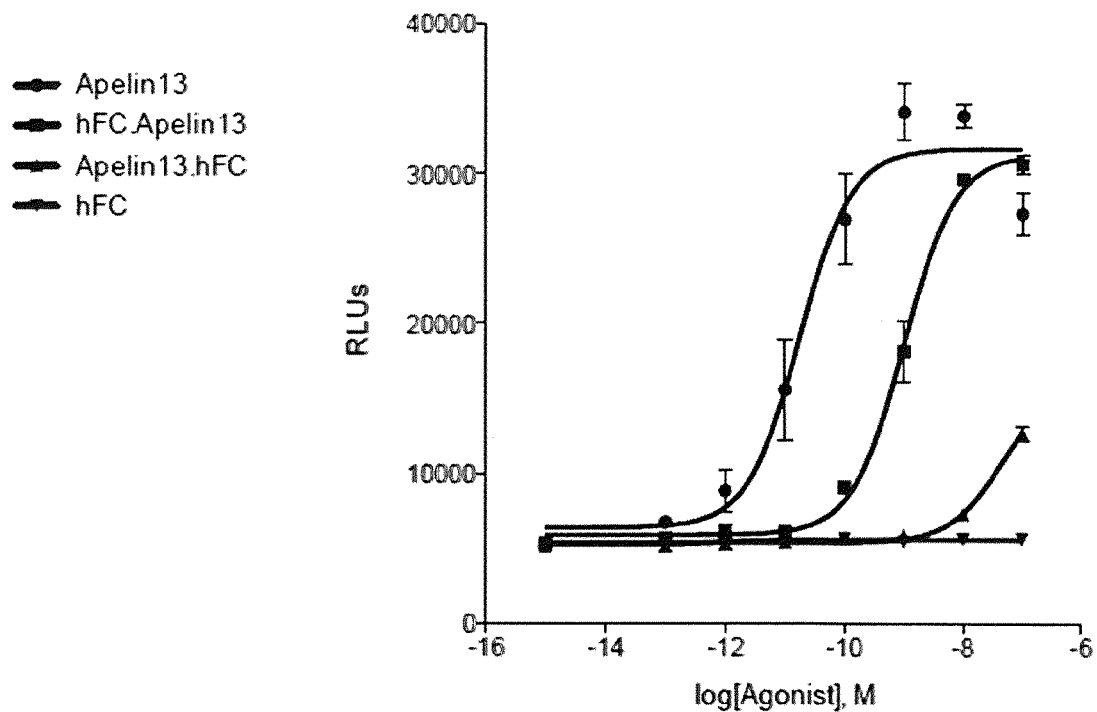
FIG. 5 represents the dose-response curve and half-maximal concentrations (EC50s) of each of the following ligands: apelin-13 (-●-), hFc-apelin13 (-■-), apelin13-hFc (-▲-), or hFc only (-▼-) in a β-arrestin assay.

The hFc-Apelin13, apelin-13, and Apelin13-hFc proteins activated CHO-K1/hAPLNR DiscoverX cells in a dose-dependent manner, with $EC_{50}$ values of 992 pM, 17.6 pM, and 44.2 nM (extrapolated value), respectively (FIG. 5).

Example 4

Potency and Efficacy of Fc Fusion Proteins in a pERK Assay

To measure the effect of the apelin-13 fusion proteins of the invention on the APLNR signaling pathway, an assay was used to quantify the amount of phosphorylated ERK1/2 (pERK1/2) and total ERK from an APLNR expressing cell line. A Chinese hamster ovary (CHO) cell line was transfected to stably express the full-length human APLNR (hAPLNR; amino acids 1-380 of accession number NP_005152.1) under the control of a doxycycline-inducible CMV promoter. The resulting cell line, CHO/hAPLNR was maintained in Ham's F12 media containing 10% FBS, penicillin/streptomycin, L-glutamine, and 250 ug/mL hygromycin B.

For the assay, CHO/hAPLNR cells were seeded onto 96 well assay plates at 10,000 cells/well in 200 µL of Ham's F12 containing 10% FBS, L-glutamine, penicillin/streptomycin and incubated at 37° C. in 5% $CO_2$ for 24 hours. The next day, to induce expression of the APLNR and prepare the cells for the pERK assay, the cells were first washed once with 250 µl of 1×PBS (Life Technologies; #20012-043), then serum-starved in Ham's F12 containing 0.1% FBS, 1% BSA, L-glutamine, penicillin/streptomycin, 0.5 µg/mL doxycycline for 24 hours. On the day of the assay, cells were treated with a 1:10 serial dilution of either unmodified apelin peptide or fusion proteins in Ham's F12 supplemented with 1% BSA, penicillin/streptomycin, L-glutamine for 15 minutes at 37° C. in 5% $CO_2$. At the end of the incubation, cells were washed with 200 µL of PBS and subsequently lysed with 100 uL of ELISAone Lysis Buffer (TGR BioSciences; #EBF001). Extracts were then analyzed for phosphorylated ERK (pERK1/2) and total ERK levels, as per the manufacturer's specifications (TGR Biosciences, #EKT001). The fluorescence signals were then measured using a Spectramax plate reader (Molecular Devices). The ratio of measured pERK1/2 to measured total ERK was calculated and the results were analyzed using GraphPad Prism.

Figure 6:
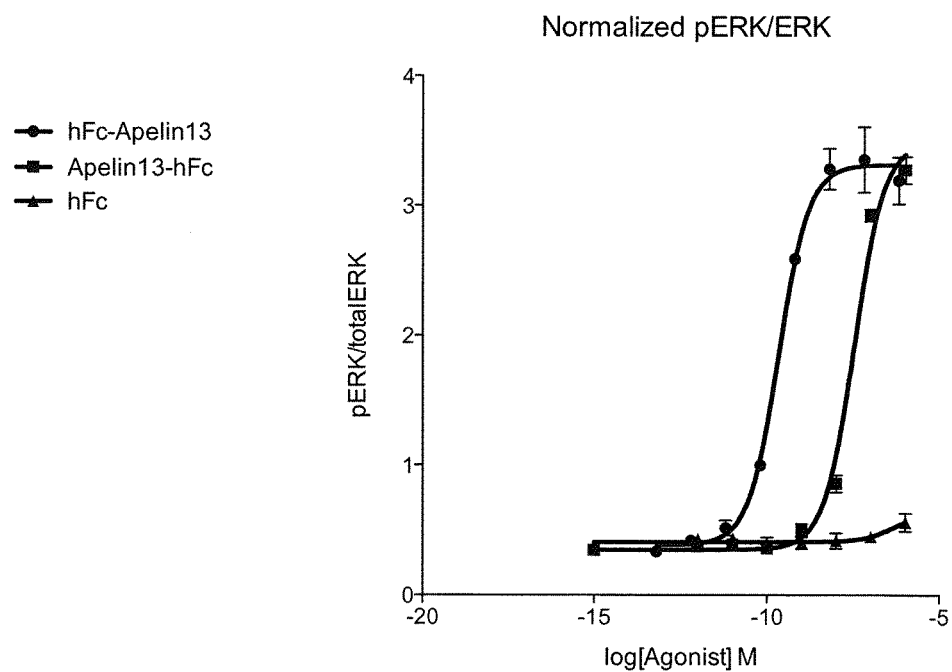
FIG. 6 represents the normalized p-ERK assay dose-response curve and half-maximal concentrations (EC50s) of hFc-apelin13 (-●-) or apelin13-hFc (-■-), compared to hFc (-▲-), showing activation of APNLR-expressing cells by both ligands.

In the pERK assay, hFc-Apelin13 and Apelin13-hFc increased the ratio of pERK1/2 to total ERK1/2 in CHO/hAPLNR cells in a dose-dependent manner, with $EC_{50}$ values of 216 µM and 33 nM, respectively (FIG. 6).

Example 6

Pharmacokinetic Study to Evaluate Serum Stability of Fc Fusions

C57/Bl6 mice (n=3 per group) were dosed subcutaneously (s.c.) with hFc (2.5 mg/kg) or Apelin13-hFc (2.8 mg/kg) (FIG. 7A) and plasma was collected at 1, 4, 24, and 48 hours. In a separate experiment, hFc-Apein13 was injected s.c. in C57/B16 mice (n=3 per group) at 5 mg/kg and serum was collected in 0, 1, 2, 4, 5, 6, 24 hours and 2, 3, 7, 14, 21 days (FIG. 7B).

To evaluate serum/plasma levels of the administered proteins, 96-well ELISA plates were coated for 18 hrs at 4° C. with a 100 µL/well of goat anti-human IgG antibody (Jackson ImmunoLab; 109-005-098) at a concentration of 1 µg/mL in PBS. The plates were subsequently blocked for 1 hour at room temperature (RT) with 300 µL/well of 1× milk diluent/blocking solution (KPL; #100108). Dilutions of hFc (for standard curve) and serum samples in 100 µL of diluent were then added to the plate. After incubating for 2 hours at RT, the wells were then washed, and plate-bound human Fc was detected by addition of a horse-radish peroxidase conjugated anti-human IgG antibody (Jackson ImmuLab; #109-035-098) to the plate for 7 minutes at RT. Samples were developed for 7 minutes with a TMB solution (MP Biomedical; #152346) to produce a colorimetric reaction and then neutralized with 100 µL/well of 2.0N $H_2SO_4$ (Mallinckrodt; #H381-05) before measuring absorbance at 450 nm wavelength on a Spectramax plate reader (Molecular Devices). Data were analyzed using SoftMax software to determine concentrations of the samples in serum.

Figure 7A:
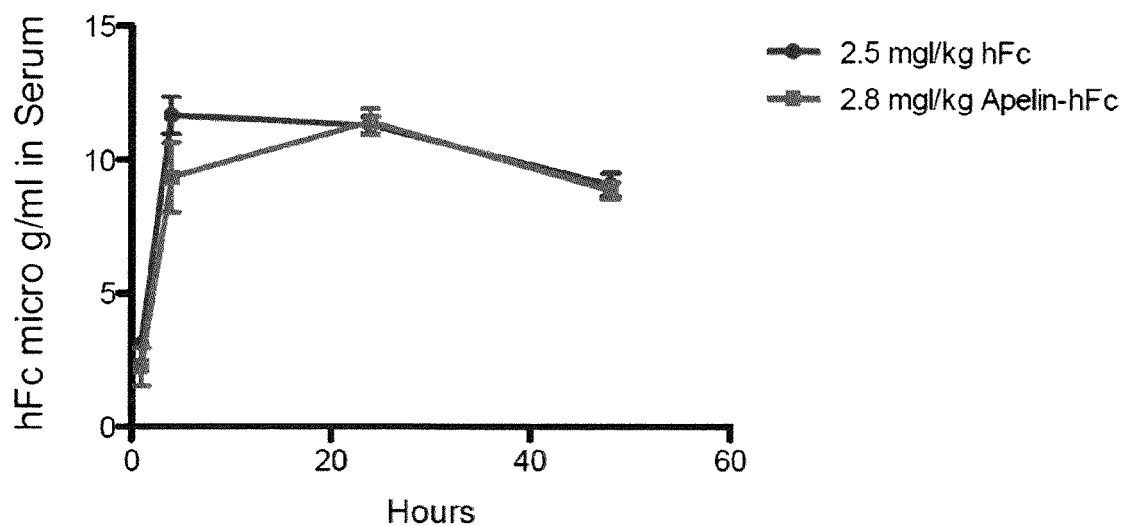
FIG. 7A shows the stability of 2.8 mg/kg apelin13-hFc (-■-) in serum of subcutaneously dosed C57/Bl6 mice, reaching levels of about 10 µg/mL for up to 48 hrs, compared to levels of hFc alone (-●-).
Figure 7B:
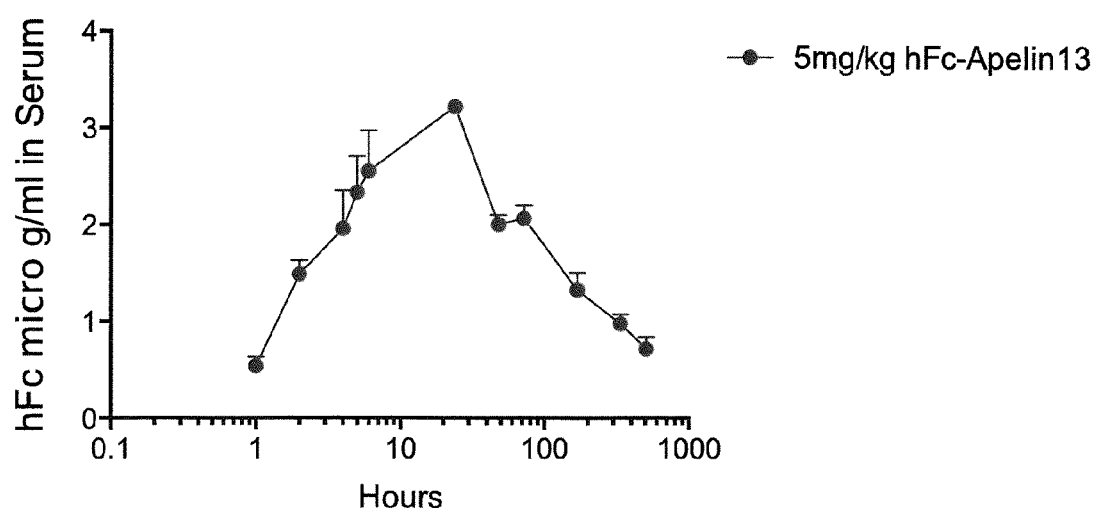
FIG. 7B shows stability of 5 mg/kg hFc-apelin13 (-●-) in serum of subcutaneously dosed C57/Bl6 mice, reaching 3 µg/mL at 24 hrs, and gradually decreasing to 1 µg/mL at about 14 days.

Apelin13-hFc serum levels reached a maximum of 10 µg/mL (380 nM) at ~4 hours and remained comparable to those of hFc after 48 hrs (FIG. 7A). The hFc-Apelin13 serum levels reached a maximum of 3 µg/mL (100 nM) at 24 hours and gradually decreased to 1 µg/mL (38 nM) at day 14 (FIG. 7B).

Example 7

Potency and Efficacy of Apelin Peptides in a CRE Assay

Apelin-13 having an Fc tethered to its N-terminus (hFc-Apelin13) displays better potency than Apelin-13 having Fc tethered to its C-terminus (Apelin-hFc), as seen in above Examples 2 through 6. Modified Apelin-13 peptides, such as Apelin-13 peptides having one or more amino acid(s) deleted from or added to the N-terminus or C-terminus, were tested for their relative potencies with respect to APLNR activation.

Modulation of cAMP levels by unmodified apelin-13 peptide (Bachem, #H-4568.0001) and modified apelin peptides of the invention were evaluated using a bioassay that was developed to detect the activation of hAPLNR, according to the method of Example 2 (supra). The results were analyzed using nonlinear regression (4-parameter logistics) with Prism 5 software (GraphPad).

As shown in Table 3, apelin-13 can tolerate deletions of amino acids from both the N-terminus and C-terminus while still retaining full efficacy, and displaying different degrees of reduced potency compared to apelin-13. Furthermore, apelin-13 can tolerate the addition of amino acid residues to its C-terminus, such as five glycine residues, and still retain full efficacy but with reduced potency, relative to apelin-13. It is envisioned that similar variations of Fc-apelin fusion proteins will maintain their efficacy.

TABLE 3

Apelin Peptides and Derivatives Maintain Efficacy in CRE Assay

| Apelin Peptide | Amino Acid Sequence | $EC_{50}$ (M) |
|---|---|---|
| Apelin-13 (SEQ ID NO: 6) | QRPRLSHKGPMPF | 1.403e-013 |
| Apelin-F13A (SEQ ID NO: 29) | QRPRLSHKGPMPA | 1.027e-010 |
| Apelin65-76 (SEQ ID NO: 30) | QRPRLSHKGPMP | 5.713e-011 |
| Apelin65-75 (SEQ ID NO: 31) | QRPRLSHKGPM | 3.604e-012 |
| Apelin-12 (SEQ ID NO: 32) | RPRLSHKGPMPF | 8.704e-013 |
| Apelin-11 (SEQ ID NO: 33) | PRLSHKGPMPF | 4.379e-010 |
| Apelin66-76 (SEQ ID NO: 34) | RPRLSHKGPMP | 5.194e-012 |
| Apelin67-76 (SEQ ID NO: 35) | PRLSHKGPMP | 1.137e-013 |
| Apelin66-75 (SEQ ID NO: 36) | RPRLSHKGPM | 2.174e-012 |
| Apelin67-75 (SEQ ID NO: 37) | PRLSHKGPM | 3.738e-007 |
| Apelin-13 + 5G (SEQ ID NO: 38) | QRPRLSHKGPMPF GGGGG | 1.469e-010 |

Example 8

Potency and Efficacy of Modified Apelin Fusion Proteins in a CRE Assay

Various apelin-Fc fusion proteins were made analogously to Example 1, except having modified apelin peptides, such as SEQ ID NO: 42, SEQ ID NO: 43 and SEQ ID NO:44, fused to the hFc. Such hFc-Apelin13 fusion proteins have an additional C-terminal amino acid at the C-terminus of the apelin peptide component. Modulation of cAMP levels by apelin-13 peptide compared to these modified Apelin-13 peptides with hFc tethered to its N-terminus (hFc-Apelin13+) were evaluated using the CRE bioassay analogously to the methods of Example 2 and Example 7 (supra). The results were analyzed using nonlinear regression (4-parameter logistics) with Prism 5 software (GraphPad).

As shown in Table 4, modified apelin fusion proteins (having an Fc at the N-terminus and additional amino acid at the C-terminus of the apelin peptide component) exhibit activity at the APLNR similar to that of unmodified apelin-13. The hFc-Apelin13 fusion protein having an additional arginine at the C-terminus activated HEK293/CRE-luc/hAPLNR cells with an $EC_{50}$ value of 60 pM. The hFc-Apelin13 fusion protein having an additional serine at the C-terminus, and the hFc-Apelin13 fusion protein having an additional histidine at the C-terminus, each activated APLNR with an $EC_{50}$ value of 96 pM and 203 pM, respectively. In this assay, apelin-13 activated with an $EC_{50}$ value of 56 pM.

TABLE 4

Modified Apelin Fusion Proteins Maintain Efficacy in CRE Assay

| Protein tested | Fusion SEQ ID NO: (apelin peptide SEQ ID NO:) | $EC_{50}$ (pM) |
|---|---|---|
| apelin-13 | — (SEQ ID NO: 6) | 56 |
| hFc-Apelin13-R | SEQ ID NO: 39 (SEQ ID NO: 42) | 60 |
| hFc-Apelin13-S | SEQ ID NO: 40 (SEQ ID NO: 43) | 96 |
| hFc-Apelin13-H | SEQ ID NO: 41 (SEQ ID NO: 44) | 203 |

Example 9

Cardiovascular Evaluation of Apelin Fc Fusions

The effects of apelin Fc-fusion proteins of the invention are assessed by electrocardiography in anesthetized mice and rats, particularly effects on RR interval (index of heart rate) as well as QT interval as an index of ion channel activity.

The effects of APLNR agonists on blood pressure, heart rate and activity by radio telemetry in mice and rats are assessed for apelin Fc-fusion proteins of the invention. This method involves the implantation of a pressure transducer in the carotid artery to measure aorta blood pressure, heart rate and activity, with continuous data monitoring.

Cardiac function is also assessed by determining changes in cardiac contractility by APLNR agonists in vivo. One method is the use of micro-ultrasound, or echocardiography (ECG) in mice or rats. Upon application of apelin Fc-fusion proteins in mice or rats, alterations in left ventricle cardiac function are monitored using measurement of left ventricle end diastolic and end systolic volumes (EDV and ESV). Other parameters are also recorded, such as ventricle diameters and heart rate, in order to calculate cardiac output (CO), Ejection Fraction (EF), Stroke Volume (SV), Fractional Shortening (FS) from recorded images of micro-ultrasound scans.

Isotropy, either induced by APNLR agonists or blocked by antagonists, is also assessed by measuring left ventricular pressure, and dP/dT (change in pressure over time), heart rate, and cardiac conductance by ECG in isolated hearts from mice or rats using a Langendorf or Working Heart system.

Myocardial ischemia/reperfusion: Effects of apelin Fc-fusion polypeptides may be assessed following myocardial ischemia/reperfusion (I/R) injury or hypoxia/re-oxygenation (H/R) in isolated rat or mouse hearts as in the Langendorf system (see e.g. Zeng, et al. 2009, *Peptides,* 30(6):1144-52, epub Feb. 24, 2009). Transient LAD ligation is performed, with apelin Fc-fusion polypeptides administered prior to reperfusion. (See e.g. Pisarenko, et al. 2011, *Bull Exp Biol Med.* 152(1):79-82.) Microultrasound measures of cardiac function (described hereinabove) are applied to determine improvement in this context. Infarct size is assessed by standard histology techniques.

Relaxation of pre-constricted aortic rings is assessed as follows: Ex vivo preparation of thoracic aorta from mouse or rat is suspended by titanium wires to a force transducer. Rings are pre-constricted with a vasoconstrictor (such as Phenylephrine, nor-epinephrine, or nor-adrenaline, endothelin or angiotensin II). An increase in diameter and a decrease in force as measured by the force transducer indicates an ability to induce vasorelaxation. (See Iturrioz, X. et al. 2010, *FASEB J,* 24(5):1506-17, Epub Dec. 29, 2009; and also the Multi Myograph system as in Zhong, et al., 2007, *Cardiovasc Res* 74(3): 388-395.)

What is claimed:

1. A polypeptide comprising the amino acid sequence of SEQ ID NO: 2.

2. A composition comprising the polypeptide of claim 1 and at least one pharmaceutically acceptable carrier or diluent.

3. A nucleic acid molecule encoding the polypeptide of claim 1.

4. The nucleic acid molecule of claim 3 linked to a nucleotide sequence encoding a signal peptide.

5. The nucleic acid molecule of claim 4 comprising the nucleotide sequence consisting of SEQ ID NO: 25.

6. A vector comprising the nucleic acid molecule of claim 5.

7. A cell comprising the vector of claim 6.

8. A cell comprising the nucleic acid molecule of claim 5.

9. The cell of claim 8, wherein the nucleic acid is stably integrated into the genome of the cell.

10. The cell of claim 9, wherein the cell is a eukaryotic cell.

11. The cell of claim 10, wherein the cell is selected from the group consisting of CHO, COS, retinal cell, Vero, CV1, 293, MDCK, HaK, BHK, HeLa, HepG2, WI38, MRC 5, Colo 25, HB 8065, HL-60, Jurkat, Daudi, A431 (epidermal), CV-1, U937, 3T3, L cell, C127 cell, SP2/0, NS-0, MMT cell, and tumor cell.

12. The cell of claim 11, wherein the cell is an animal cell.

13. The cell of claim 12, wherein the cell is a mammalian cell.

14. The cell of claim 13, wherein the cell is a CHO cell.

15. The cell of claim 14, wherein the cell is a CHO-K1 cell.

* * * * *

SEQUENCE LISTING

```
<160> NUMBER OF SEQ ID NOS: 44

<210> SEQ ID NO 1
<211> LENGTH: 293
<212> TYPE: PRT
<213> ORGANISM: Artificial Sequence
<220> FEATURE:
<223> OTHER INFORMATION: Synthetic

<400> SEQUENCE: 1

Met His Arg Pro Arg Arg Gly Thr Arg Pro Pro Leu Ala Leu
1               5                  10                  15

Leu Ala Ala Leu Leu Leu Ala Ala Arg Gly Ala Asp Ala Arg Ser Thr
                20                  25                  30

Gly Ser Pro Gly Ser Gly Asp Lys Thr His Thr Cys Pro Pro Cys Pro
            35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys Gly Gly Gly Ser Gly Gly
            260                 265                 270

Gly Gly Ser Gly Gly Gly Ser Gln Arg Pro Arg Leu Ser His Lys
        275                 280                 285
```

```
Gly Pro Met Pro Phe
        290

<210> SEQ ID NO 2
<211> LENGTH: 255
<212> TYPE: PRT
<213> ORGANISM: Artificial Sequence
<220> FEATURE:
<223> OTHER INFORMATION: Synthetic

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gly Gly
225                 230                 235                 240

Gly Ser Gln Arg Pro Arg Leu Ser His Lys Gly Pro Met Pro Phe
                245                 250                 255

<210> SEQ ID NO 3
<211> LENGTH: 284
<212> TYPE: PRT
<213> ORGANISM: Artificial Sequence
<220> FEATURE:
<223> OTHER INFORMATION: Synthetic

<400> SEQUENCE: 3

Met His Arg Pro Arg Arg Arg Gly Thr Arg Pro Pro Leu Ala Leu
1               5                   10                  15

Leu Ala Ala Leu Leu Leu Ala Ala Arg Gly Ala Asp Ala Gln Arg Pro
            20                  25                  30

Arg Leu Ser His Lys Gly Pro Met Pro Phe Gly Gly Gly Ser Gly
        35                  40                  45
```

Gly Gly Gly Ser Gly Gly Gly Ser Asp Lys Thr His Thr Cys Pro
            50                  55                  60
Pro Cys Pro Ala Pro Glu Leu Leu Gly Gly Pro Ser Val Phe Leu Phe
 65                  70                  75                  80
Pro Pro Lys Pro Lys Asp Thr Leu Met Ile Ser Arg Thr Pro Glu Val
                85                  90                  95
Thr Cys Val Val Val Asp Val Ser His Glu Asp Pro Glu Val Lys Phe
            100                 105                 110
Asn Trp Tyr Val Asp Gly Val Glu Val His Asn Ala Lys Thr Lys Pro
        115                 120                 125
Arg Glu Glu Gln Tyr Asn Ser Thr Tyr Arg Val Val Ser Val Leu Thr
130                 135                 140
Val Leu His Gln Asp Trp Leu Asn Gly Lys Glu Tyr Lys Cys Lys Val
145                 150                 155                 160
Ser Asn Lys Ala Leu Pro Ala Pro Ile Glu Lys Thr Ile Ser Lys Ala
                165                 170                 175
Lys Gly Gln Pro Arg Glu Pro Gln Val Tyr Thr Leu Pro Pro Ser Arg
            180                 185                 190
Asp Glu Leu Thr Lys Asn Gln Val Ser Leu Thr Cys Leu Val Lys Gly
        195                 200                 205
Phe Tyr Pro Ser Asp Ile Ala Val Glu Trp Glu Ser Asn Gly Gln Pro
210                 215                 220
Glu Asn Asn Tyr Lys Thr Thr Pro Pro Val Leu Asp Ser Asp Gly Ser
225                 230                 235                 240
Phe Phe Leu Tyr Ser Lys Leu Thr Val Asp Lys Ser Arg Trp Gln Gln
                245                 250                 255
Gly Asn Val Phe Ser Cys Ser Val Met His Glu Ala Leu His Asn His
            260                 265                 270
Tyr Thr Gln Lys Ser Leu Ser Leu Ser Pro Gly Lys
        275                 280

<210> SEQ ID NO 4
<211> LENGTH: 255
<212> TYPE: PRT
<213> ORGANISM: Artificial Sequence
<220> FEATURE:
<223> OTHER INFORMATION: Synthetic

<400> SEQUENCE: 4

Gln Arg Pro Arg Leu Ser His Lys Gly Pro Met Pro Phe Gly Gly Gly
 1               5                  10                  15
Gly Ser Gly Gly Gly Gly Ser Gly Gly Gly Ser Asp Lys Thr His
            20                  25                  30
Thr Cys Pro Pro Cys Pro Ala Pro Glu Leu Leu Gly Gly Pro Ser Val
            35                  40                  45
Phe Leu Phe Pro Pro Lys Pro Lys Asp Thr Leu Met Ile Ser Arg Thr
    50                  55                  60
Pro Glu Val Thr Cys Val Val Val Asp Val Ser His Glu Asp Pro Glu
 65                  70                  75                  80
Val Lys Phe Asn Trp Tyr Val Asp Gly Val Glu Val His Asn Ala Lys
                85                  90                  95
Thr Lys Pro Arg Glu Glu Gln Tyr Asn Ser Thr Tyr Arg Val Val Ser
            100                 105                 110
Val Leu Thr Val Leu His Gln Asp Trp Leu Asn Gly Lys Glu Tyr Lys
        115                 120                 125

```
Cys Lys Val Ser Asn Lys Ala Leu Pro Ala Pro Ile Glu Lys Thr Ile
            130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys
                245                 250                 255

<210> SEQ ID NO 5
<211> LENGTH: 77
<212> TYPE: PRT
<213> ORGANISM: Homo sapiens

<400> SEQUENCE: 5

Met Asn Leu Arg Leu Cys Val Gln Ala Leu Leu Leu Trp Leu Ser
1               5                   10                  15

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
        35                  40                  45

Arg Asn Gly Pro Gly Pro Trp Gln Gly Gly Arg Arg Lys Phe Arg Arg
    50                  55                  60

Gln Arg Pro Arg Leu Ser His Lys Gly Pro Met Pro Phe
65                  70                  75

<210> SEQ ID NO 6
<211> LENGTH: 13
<212> TYPE: PRT
<213> ORGANISM: Homo sapiens

<400> SEQUENCE: 6

Gln Arg Pro Arg Leu Ser His Lys Gly Pro Met Pro Phe
1               5                   10

<210> SEQ ID NO 7
<211> LENGTH: 17
<212> TYPE: PRT
<213> ORGANISM: Homo sapiens

<400> SEQUENCE: 7

Lys Phe Arg Arg Gln Arg Pro Arg Leu Ser His Lys Gly Pro Met Pro
1               5                   10                  15

Phe

<210> SEQ ID NO 8
<211> LENGTH: 36
<212> TYPE: PRT
<213> ORGANISM: Homo sapiens

<400> SEQUENCE: 8
```

```
Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
                20                  25                  30

Pro Met Pro Phe
        35

<210> SEQ ID NO 9
<211> LENGTH: 29
<212> TYPE: PRT
<213> ORGANISM: Mus musculus

<400> SEQUENCE: 9

Met His Arg Pro Arg Arg Gly Thr Arg Pro Pro Leu Ala Leu
1               5                   10                  15

Leu Ala Ala Leu Leu Ala Ala Arg Gly Ala Asp Ala
                20                  25

<210> SEQ ID NO 10
<211> LENGTH: 937
<212> TYPE: PRT
<213> ORGANISM: Mus musculus

<400> SEQUENCE: 10

Met His Arg Pro Arg Arg Gly Thr Arg Pro Pro Leu Ala Leu
1               5                   10                  15

Leu Ala Ala Leu Leu Ala Ala Arg Gly Ala Asp Ala Gln Glu Thr
                20                  25                  30

Glu Leu Ser Val Ser Ala Glu Leu Val Pro Thr Ser Ser Trp Asn Thr
                35                  40                  45

Ser Ser Glu Ile Asp Lys Gly Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Ser Ile Arg Trp Phe Lys Asn Asp Ala
                85                  90                  95

Pro Val Val Gln Glu Pro Arg Arg Ile Ser Phe Arg Ala Thr Asn Tyr
                100                 105                 110

Gly Ser Arg Leu Arg Ile Arg Asn Leu Asp Thr Thr Asp Thr Gly Tyr
                115                 120                 125

Phe Gln Cys Val Ala Thr Asn Gly Lys Lys Val Val Ser Thr Thr Gly
        130                 135                 140

Val Leu Phe Val Lys Phe Gly Pro Pro Thr Ala Ser Pro Gly Ser
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
                180                 185                 190

His Met Gln Gly Glu Ile Glu Asn Gln Ile Thr Ala Ala Phe Thr Met
                195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Val Leu Glu
                245                 250                 255
```

-continued

```
Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Ser Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Phe Leu Phe Phe Phe Ile Cys Val Cys Arg Asn Asn Gln
            420                 425                 430

Lys Ser Ser Ser Pro Pro Val Gln Arg Gln Pro Lys Pro Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Thr Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Met Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Ser Leu Pro Ile
                645                 650                 655

Arg Trp Met Pro Pro Glu Ala Ile Met Tyr Gly Lys Phe Ser Ser Asp
            660                 665                 670
```

```
                                   -continued

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Phe Pro Asn Tyr Met Phe Pro Ser Gln Gly Ile Thr Pro Gln Gly
785                 790                 795                 800

Gln Ile Ala Gly Phe Ile Gly Pro Ala Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Ala Gly Pro Pro Arg Val Ile Gln His Cys
        835                 840                 845

Pro Pro Pro Lys Ser Arg Ser Pro Ser Ser Ala Arg Gly Ser Thr Ser
    850                 855                 860

Thr Gly His Val Ala Ser Leu Pro Ser Ser Gly Ser Asn Gln Glu Ala
865                 870                 875                 880

Asn Val Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ser Ser Leu Leu Gly Asp Ser His Ile His Gly His
        915                 920                 925

Thr Glu Ser Met Ile Ser Ala Glu Val
    930                 935

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Arg Ser Thr Gly Ser Pro Gly Ser Gly
1               5

<210> SEQ ID NO 13
```

<211> LENGTH: 227
<212> TYPE: PRT
<213> ORGANISM: Homo sapiens

<400> SEQUENCE: 13

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 14
<211> LENGTH: 16
<212> TYPE: PRT
<213> ORGANISM: Homo sapiens

<400> SEQUENCE: 14

```
Asp Lys Thr His Thr Cys Pro Pro Cys Pro Ala Pro Glu Leu Leu Gly
1               5                   10                  15
```

<210> SEQ ID NO 15
<211> LENGTH: 104
<212> TYPE: PRT
<213> ORGANISM: Homo sapiens

<400> SEQUENCE: 15

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45
```

```
His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
 65                  70                  75                  80

Lys Glu Tyr Lys Cys Lys Val Ser Asn Lys Ala Leu Pro Ala Pro Ile
                 85                  90                  95

Glu Lys Thr Ile Ser Lys Ala Lys
            100
```

<210> SEQ ID NO 16
<211> LENGTH: 107
<212> TYPE: PRT
<213> ORGANISM: Homo sapiens

<400> SEQUENCE: 16

```
Gly Gln Pro Arg Glu Pro Gln Val Tyr Thr Leu Pro Pro Ser Arg Asp
  1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 17
<211> LENGTH: 17
<212> TYPE: PRT
<213> ORGANISM: Homo sapiens

<400> SEQUENCE: 17

```
Glu Arg Lys Cys Cys Val Glu Cys Pro Pro Cys Pro Ala Pro Pro Val
  1               5                  10                  15

Ala
```

<210> SEQ ID NO 18
<211> LENGTH: 10
<212> TYPE: PRT
<213> ORGANISM: Homo sapiens

<400> SEQUENCE: 18

```
Cys Pro Pro Cys Pro Ala Pro Pro Val Ala
  1               5                  10
```

<210> SEQ ID NO 19
<211> LENGTH: 104
<212> TYPE: PRT
<213> ORGANISM: Homo sapiens

<400> SEQUENCE: 19

```
Gly Pro Ser Val Phe Leu Phe Pro Pro Lys Pro Lys Asp Thr Leu Met
  1               5                  10                  15

Ile Ser Arg Thr Pro Glu Val Thr Cys Val Val Val Asp Val Ser His
                 20                  25                  30
```

Glu Asp Pro Glu Val Gln Phe Asn Trp Tyr Val Asp Val Glu Val
            35                  40                  45

His Asn Ala Lys Thr Lys Pro Arg Glu Gln Phe Asn Ser Thr Phe
 50                  55                  60

Arg Val Val Ser Val Leu Thr Val Val His Gln Asp Trp Leu Asn Gly
 65                  70                  75                  80

Lys Glu Tyr Lys Cys Lys Val Ser Asn Lys Gly Leu Pro Ala Pro Ile
                 85                  90                  95

Glu Lys Thr Ile Ser Lys Thr Lys
                100

<210> SEQ ID NO 20
<211> LENGTH: 107
<212> TYPE: PRT
<213> ORGANISM: Homo sapiens

<400> SEQUENCE: 20

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
                 20                  25                  30

Tyr Pro Ser Asp Ile Ser Val Glu Trp Glu Ser Asn Gly Gln Pro Glu
             35                  40                  45

Asn Asn Tyr Lys Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
                100                 105

<210> SEQ ID NO 21
<211> LENGTH: 18
<212> TYPE: PRT
<213> ORGANISM: Homo sapiens

<400> SEQUENCE: 21

Glu Ser Lys Tyr Gly Pro Pro Cys Pro Ser Cys Pro Ala Pro Glu Phe
 1               5                  10                  15

Leu Gly

<210> SEQ ID NO 22
<211> LENGTH: 13
<212> TYPE: PRT
<213> ORGANISM: Homo sapiens

<400> SEQUENCE: 22

Pro Pro Cys Pro Ser Cys Pro Ala Pro Glu Phe Leu Gly
 1               5                  10

<210> SEQ ID NO 23
<211> LENGTH: 104
<212> TYPE: PRT
<213> ORGANISM: Homo sapiens

<400> SEQUENCE: 23

Gly Pro Ser Val Phe Leu Phe Pro Pro Lys Pro Lys Asp Thr Leu Met
 1               5                  10                  15

Ile Ser Arg Thr Pro Glu Val Thr Cys Val Val Val Asp Val Ser Gln
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Gly Leu Pro Ser Ser Ile
                85                  90                  95

Glu Lys Thr Ile Ser Lys Ala Lys
            100

<210> SEQ ID NO 24
<211> LENGTH: 107
<212> TYPE: PRT
<213> ORGANISM: Homo sapiens

<400> SEQUENCE: 24

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 25
<211> LENGTH: 882
<212> TYPE: DNA
<213> ORGANISM: Artificial Sequence
<220> FEATURE:
<223> OTHER INFORMATION: Synthetic

<400> SEQUENCE: 25
atgcacagac ctagacgtcg tggaactcgt ccacctccac tggcactgct cgctgctctc      60
ctcctggctg cacgtggtgc tgatgcaaga tctaccggta gcccgggctc cggagacaaa     120
actcacacat gcccaccgtg cccagcacct gaactcctgg ggggaccgtc agtcttcctc     180
ttccccccaa aacccaagga caccctcatg atctcccgga cccctgaggt cacatgcgtg     240
gtggtggacg tgagccacga agaccctgag gtcaagttca actggtacgt ggacggcgtg     300
gaggtgcata atgccaagac aaagccgcgg gaggagcagt acaacagcac gtaccgtgtg     360
gtcagcgtcc tcaccgtcct gcaccaggac tggctgaatg gcaaggagta caagtgcaag     420
gtctccaaca aagccctccc agcccccatc gagaaaacca tctccaaagc caagggcag     480 ccccgagaac cacaggtgta caccctgccc ccatcccggg atgagctgac caagaaccag     540
gtcagcctga cctgcctggt caaaggcttc tatcccagcg acatcgccgt ggagtgggag     600
agcaatgggc agccggagaa caactacaag accacgcctc ccgtgctgga ctccgacggc     660

```
tccttcttcc tctacagcaa gctcaccgtg acaagagca ggtggcagca ggggaacgtc    720
ttctcatgct ccgtgatgca tgaggctctg cacaaccact acacgcagaa gtccctctcc    780
ctgtctccgg gtaaaggtgg aggcggttca ggcggaggtg gctctggcgg tggcggatcg    840
cagaggccca ggctgagcca aagggcccc atgcccttct ga    882
```

<210> SEQ ID NO 26
<211> LENGTH: 855
<212> TYPE: DNA
<213> ORGANISM: Artificial Sequence
<220> FEATURE:
<223> OTHER INFORMATION: Synthetic

<400> SEQUENCE: 26

```
atgcacagac ctagacgtcg tggaactcgt ccacctccac tggcactgct cgctgctctc     60
ctcctggctg cacgtggtgc tgatgcacag aggcccaggc tgagccacaa gggccccatg    120
cccttcggtg gaggcggttc aggcggaggt ggctctggcg gtggcggatc ggacaaaact    180
cacacatgcc caccgtgccc agcacctgaa ctcctggggg gaccgtcagt cttcctcttc    240
cccccaaaac ccaaggacac cctcatgatc tcccggaccc ctgaggtcac atgcgtggtg    300
gtggacgtga gccacgaaga ccctgaggtc aagttcaact ggtacgtgga cggcgtggag    360
gtgcataatg ccaagacaaa gccgcgggag gagcagtaca acagcacgta ccgtgtggtc    420
agcgtcctca ccgtcctgca ccaggactgg ctgaatggca aggagtacaa gtgcaaggtc    480
tccaacaaag ccctcccagc ccccatcgag aaaaccatct ccaaagccaa agggcagccc    540
cgagaaccac aggtgtacac cctgcccca tcccgggatg agctgaccaa gaaccaggtc    600
agcctgacct gcctggtcaa aggcttctat ccagcgaca tcgccgtgga gtgggagagc    660
aatgggcagc cggagaacaa ctacaagacc acgcctcccg tgctggactc cgacggctcc    720
ttcttcctct acagcaagct caccgtggac aagagcaggt ggcagcaggg gaacgtcttc    780
tcatgctccg tgatgcatga ggctctgcac aaccactaca cgcagaagtc cctctccctg    840
tctccgggta aatag    855
```

<210> SEQ ID NO 27
<211> LENGTH: 768
<212> TYPE: DNA
<213> ORGANISM: Artificial Sequence
<220> FEATURE:
<223> OTHER INFORMATION: Synthetic

<400> SEQUENCE: 27

```
gacaaaactc acacatgccc accgtgccca gcacctgaac tcctgggggg accgtcagtc     60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc cagcgacat cgccgtggag    480 tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaagtcc    660
```

```
ctctccctgt ctccgggtaa aggtggaggc ggttcaggcg aggtggctc tggcggtggc    720 ggatcgcaga ggcccaggct gagccacaag ggccccatgc ccttctga               768
```

<210> SEQ ID NO 28
<211> LENGTH: 768
<212> TYPE: DNA
<213> ORGANISM: Artificial Sequence
<220> FEATURE:
<223> OTHER INFORMATION: Synthetic

<400> SEQUENCE: 28

```
cagaggccca ggctgagcca agggcccc atgcccttcg gtggaggcgg ttcaggcgga     60
ggtggctctg gcggtggcgg atcggacaaa actcacacat gcccaccgtg cccagcacct  120
gaactcctgg gggaccgtc agtcttcctc ttccccccaa acccaagga caccctcatg    180 atctcccgga cccctgaggt cacatgcgtg gtggtggacg tgagccacga agaccctgag  240
gtcaagttca actggtacgt ggacggcgtg gaggtgcata atgccaagac aaagccgcgg  300
gaggagcagt acaacagcac gtaccgtgtg gtcagcgtcc tcaccgtcct gcaccaggac  360
tggctgaatg gcaaggagta caagtgcaag gtctccaaca aagccctccc agcccccatc  420
gagaaaacca tctccaaagc caaagggcag ccccgagaac acaggtgta caccctgccc   480 ccatcccggg atgagctgac caagaaccag gtcagcctga cctgcctggt caaaggcttc  540
tatcccagcg acatcgccgt ggagtgggag agcaatgggc agccggagaa caactacaag  600
accacgcctc ccgtgctgga ctccgacggc tccttcttcc tctacagcaa gctcaccgtg  660
gacaagagca ggtggcagca ggggaacgtc ttctcatgct ccgtgatgca tgaggctctg  720
cacaaccact acacgcagaa gtccctctcc ctgtctccgg gtaaatag               768
```

<210> SEQ ID NO 29
<211> LENGTH: 13
<212> TYPE: PRT
<213> ORGANISM: Artificial Sequence
<220> FEATURE:
<223> OTHER INFORMATION: Synthetic

<400> SEQUENCE: 29

Gln Arg Pro Arg Leu Ser His Lys Gly Pro Met Pro Ala
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic

<400> SEQUENCE: 30

Gln Arg Pro Arg Leu Ser His Lys Gly Pro Met Pro
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Gln Arg Pro Arg Leu Ser His Lys Gly Pro Met
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Arg Pro Arg Leu Ser His Lys Gly Pro Met Pro Phe
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Pro Arg Leu Ser His Lys Gly Pro Met Pro Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic

<400> SEQUENCE: 34

Arg Pro Arg Leu Ser His Lys Gly Pro Met Pro
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Pro Arg Leu Ser His Lys Gly Pro Met Pro
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Arg Pro Arg Leu Ser His Lys Gly Pro Met
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic

<400> SEQUENCE: 37

Pro Arg Leu Ser His Lys Gly Pro Met
1               5

<210> SEQ ID NO 38
<211> LENGTH: 18
<212> TYPE: PRT
<213> ORGANISM: Artificial Sequence
<220> FEATURE:
<223> OTHER INFORMATION: Synthetic

<400> SEQUENCE: 38

Gln Arg Pro Arg Leu Ser His Lys Gly Pro Met Pro Phe Gly Gly Gly
1               5                   10                  15

Gly Gly

<210> SEQ ID NO 39
<211> LENGTH: 256
<212> TYPE: PRT
<213> ORGANISM: Artificial Sequence
<220> FEATURE:
<223> OTHER INFORMATION: Synthetic

<400> SEQUENCE: 39

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Gly Gly Gly Gly
225                 230                 235                 240

Gly Ser Gln Arg Pro Arg Leu Ser His Lys Gly Pro Met Pro Phe Arg
                245                 250                 255

<210> SEQ ID NO 40
<211> LENGTH: 256
<212> TYPE: PRT
<213> ORGANISM: Artificial Sequence
<220> FEATURE:

<223> OTHER INFORMATION: Synthetic

<400> SEQUENCE: 40

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Gly Gly Gly Gly
225                 230                 235                 240

Gly Ser Gln Arg Pro Arg Leu Ser His Lys Gly Pro Met Pro Phe Ser
                245                 250                 255

<210> SEQ ID NO 41
<211> LENGTH: 256
<212> TYPE: PRT
<213> ORGANISM: Artificial Sequence
<220> FEATURE:
<223> OTHER INFORMATION: Synthetic

<400> SEQUENCE: 41

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Gly Gly Ser Gly Gly Gly Ser Gly Gly Gly Gly
225                 230                 235                 240
Gly Ser Gln Arg Pro Arg Leu Ser His Lys Gly Pro Met Pro Phe His
                245                 250                 255

<210> SEQ ID NO 42
<211> LENGTH: 14
<212> TYPE: PRT
<213> ORGANISM: Artificial Sequence
<220> FEATURE:
<223> OTHER INFORMATION: Synthetic

<400> SEQUENCE: 42

Gln Arg Pro Arg Leu Ser His Lys Gly Pro Met Pro Phe Arg
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Gln Arg Pro Arg Leu Ser His Lys Gly Pro Met Pro Phe Ser
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic

<400> SEQUENCE: 44

Gln Arg Pro Arg Leu Ser His Lys Gly Pro Met Pro Phe His
1               5                   10
```